United States Patent
Lawandy

[11] Patent Number: 5,825,790
[45] Date of Patent: Oct. 20, 1998

[54] OPTICAL SOURCES HAVING A STRONGLY SCATTERING GAIN MEDIUM PROVIDING LASER-LIKE ACTION

[75] Inventor: Nabil M. Lawandy, Providence, R.I.

[73] Assignee: Brown University Research Foundation, Providence, R.I.

[21] Appl. No.: 745,494

[22] Filed: Nov. 12, 1996

Related U.S. Application Data

[62] Division of Ser. No. 401,356, Mar. 9, 1995, Pat. No. 5,625,456, which is a division of Ser. No. 210,710, Mar. 18, 1994, Pat. No. 5,448,582.

[51] Int. Cl.$^6$ .................................................. H01S 3/10
[52] U.S. Cl. ................................................................. 372/23
[58] Field of Search ................................. 372/42, 12, 19, 372/23, 24, 68, 82, 108

[56] References Cited

U.S. PATENT DOCUMENTS

| | | | |
|---|---|---|---|
| H437 | 2/1988 | Conrad | 372/53 |
| H483 | 6/1988 | Moran et al. | 372/53 |
| 3,706,051 | 12/1972 | Collier et al. | 331/94.5 |
| 3,745,484 | 7/1973 | Caristi | 331/94.5 |
| 3,818,371 | 6/1974 | Herz et al. | 331/94.5 |
| 3,938,058 | 2/1976 | Yamamoto | 331/94.5 |
| 4,229,078 | 10/1980 | Bly et al. | 350/353 |
| 4,301,426 | 11/1981 | Schneider | 331/94.5 |
| 4,519,082 | 5/1985 | Schneider | 372/42 |
| 4,646,308 | 2/1987 | Kafka et al. | 372/25 |
| 4,672,619 | 6/1987 | Luty et al. | 372/42 |
| 4,685,802 | 8/1987 | Saito et al. | 356/339 |
| 4,767,205 | 8/1988 | Schwartertel | 356/71 |
| 4,853,937 | 8/1989 | Rinke et al. | 372/53 |
| 4,878,224 | 10/1989 | Kuder et al. | 372/53 |
| 4,964,133 | 10/1990 | Pollock et al. | 372/42 |
| 5,023,139 | 6/1991 | Birnboim et al. | 428/402 |
| 5,121,398 | 6/1992 | Rao | 372/20 |
| 5,157,674 | 10/1992 | Lawandy | 372/22 |
| 5,233,621 | 8/1993 | Lawandy | 372/22 |
| 5,237,582 | 8/1993 | Moses | 372/53 |
| 5,253,258 | 10/1993 | Lawandy | 372/22 |
| 5,422,489 | 6/1995 | Bhargava | 250/488.1 |
| 5,434,878 | 7/1995 | Lawandy | 372/43 |

FOREIGN PATENT DOCUMENTS

| | | | |
|---|---|---|---|
| 63-233592 (A) | 9/1988 | Japan | H01S 3/20 |

OTHER PUBLICATIONS

"Non–Resonant Feedback in Lasers" by R.V. Ambartsumyan, N.G. Basov, P.G. Kryukov and V.S. Letokhov, Science Library, copyright 1970, No Month.

"Brillouin and Rayleigh Scattering in Aprotic Laser Solutions Containing Neodymium" by R. Pappalardo and A. Lempicki, Jrnl. Appl. Phys. vol., 43, No. 4, Apr. 1972, pp. 1699–1708.

(List continued on next page.)

*Primary Examiner*—Leon Scott, Jr.
*Assistant Examiner*—Robert E. Wise
*Attorney, Agent, or Firm*—Perman & Green, LLP

[57] ABSTRACT

A gain medium is comprised of a multi-phase system wherein: a first phase is an electromagnetic radiation emission phase; a second phase is an electromagnetic radiation scattering phase; and a third phase is a transparent matrix phase. By example, the emission phase may consist of dye molecules, the scattering phase may consist of high contrast particles, and the matrix phase may consist of a solvent such as methanol. In some embodiments of this invention the emission and scattering phases may be the same phase, as when semiconductor particles are employed. A smallest dimension of a body comprised of the gain medium may be less than a scattering length associated with the scattering phase. It is shown that nearly thresholdless laser behavior is observed in strongly scattering optically pumped dye-methanol solutions containing colloidal $TiO_2$ or $Al_2O_3$ ruby nanoparticles. The emission from the high gain colloid exhibits a slope change in the linear input-output characteristics above a critical pump pulse energy. The change in slope is accompanied by a spectral line narrowing with a bichromatic spectrum appearing at high pump energies.

13 Claims, 17 Drawing Sheets

OTHER PUBLICATIONS

"Airborne Laser Radar for Mapping Two–Dimensional Contours of Aerosol Concentration" by G.W. Grams, E.M. Patterson and C.M. Wyman, Optical and Quantum Electronics, No. 3, May 1975, pp. 187–191.

"Synthesis and Characterization of Nearly Monodisperse CdE (E=S, Se, Te) Semiconductor Nanocrystallites", by C.B. Murray, D.M. Norris, and M.G. Bawendi, Jrnl. Am. Chem. Soc. 1993, 115, Mar. 22, 1993, pp. 8706–8715.

"Stimulated Emission of an Ensemble of Scattering Particles with Negative Absorption", by V.S. Letokhov, USSR Academy of Science, 10 Feb. 1967.

"Transmission Losses in Aprotic Liquid Lasers", C. Brecher, K. French, W. Watson, and D. Miller, Jrnl. of Applied Physics, vol. 41, No. 11, Oct. 1970, pp. 4578–4581.

"Laser Liquid", Sylvania Precision Materials, Towanda, PA (Temporary Data Sheet), Jun. 3, 1970.

"Generation of Light by a Scattering Medium with Negative Resonance Absorption", Sov. Phys. JETP. vol. 26, No. 4, Apr. 1968, pp. 835–839.

"Generation of Simulated Noncoherent Radiation in Light-–Scattering Media Exhibiting Chemical Reactions", Sov. J. Quantum Electron, 12(5), May 1982, pp. 588–594.

"Optical Properties of Maganese–Doped Nanocrystals of ZnS", in the American Physical Society, vol. 72, No. 3, Jan. 19, 1994, by R. N. Bhargava and D. Gallagher.

"Doped Nanocrystals of Semiconductors–A New Class of Luninescent Materials" 1993 International Conference on Luminescence, THIB–2, Aug. 9–13, 1993, Univ. of Conn. by R. N. Bhargava.

TIME (2 nanoseconds/div)

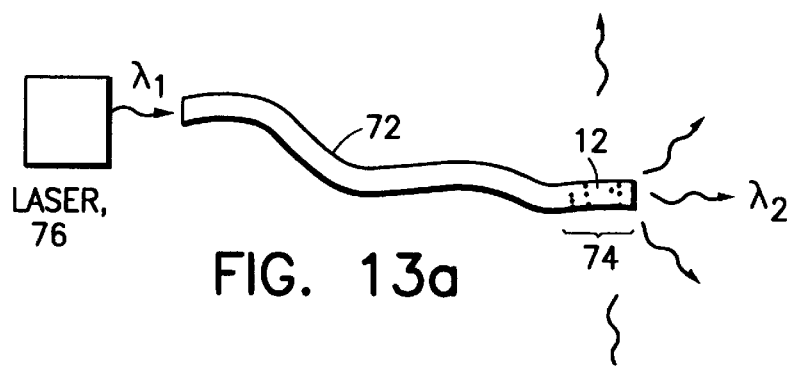
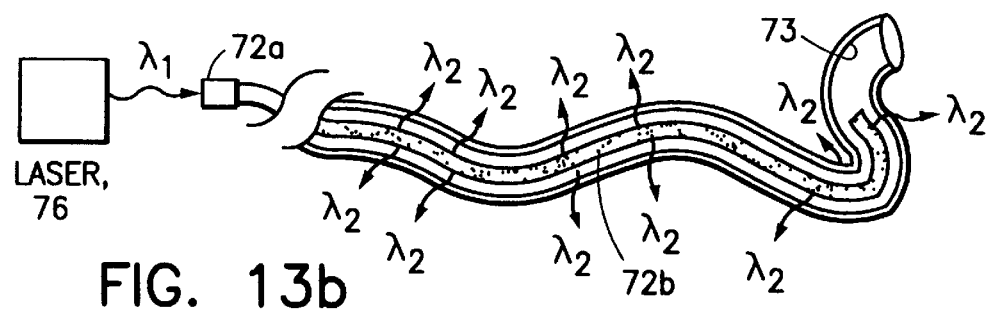
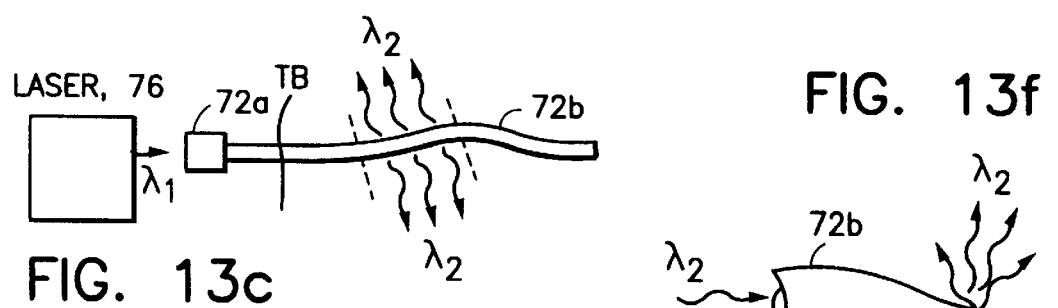
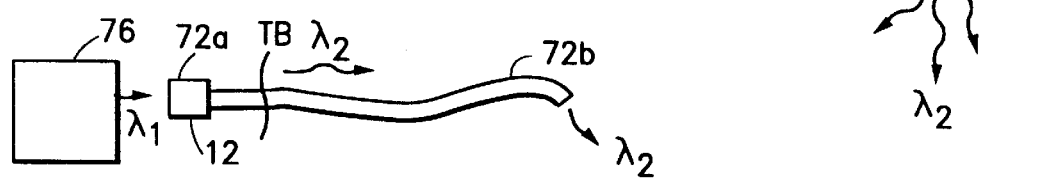
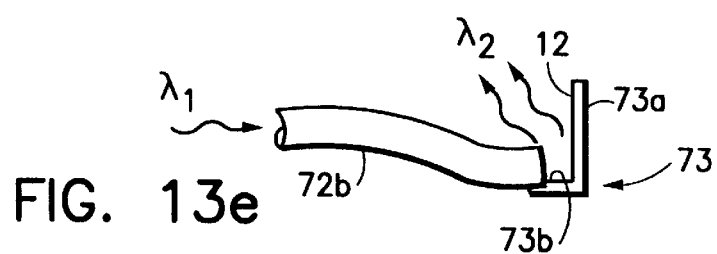

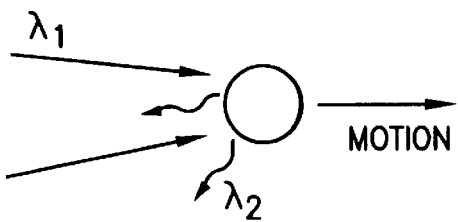
FIG. 21
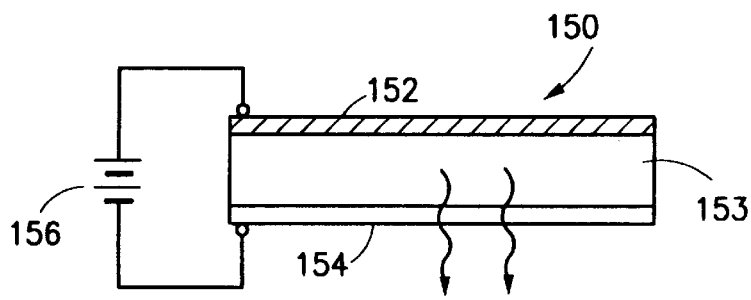
FIG. 22
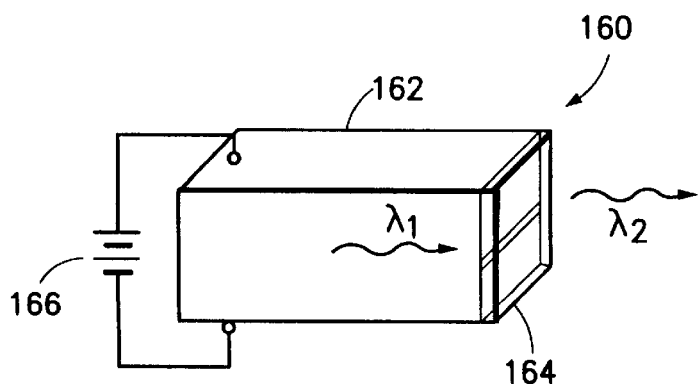
FIG. 23
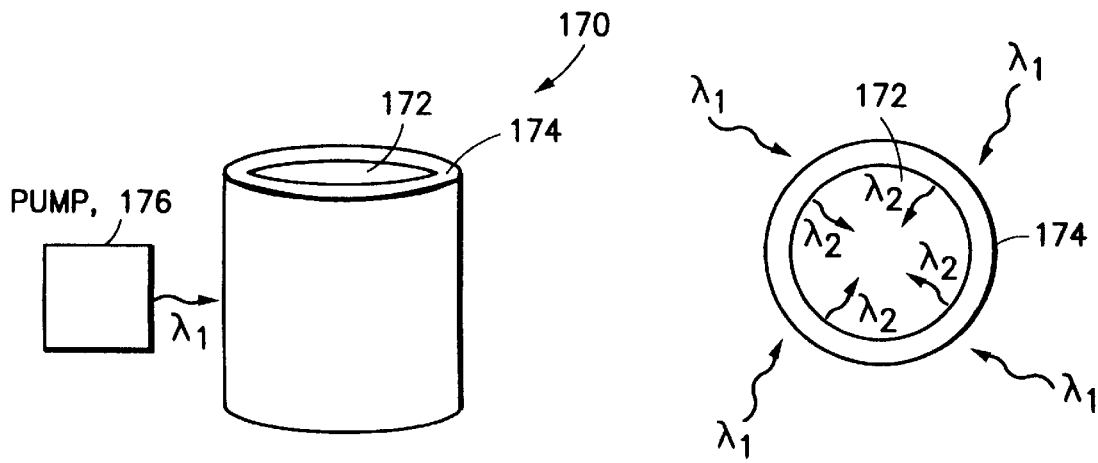
FIG. 24a
FIG. 24b

OPTICAL SOURCES HAVING A STRONGLY SCATTERING GAIN MEDIUM PROVIDING LASER-LIKE ACTION

This is a divisional of copending application Ser. No. 08/401,356, now U.S. Pat. No. 5,625,456 filed Mar. 9, 1995, which is a division of Ser. No. 210,710 filed Mar. 18, 1994, now U.S. Pat. No. 5,448,582.

CROSS-REFERENCE TO A RELATED PATENT APPLICATION

This patent application is related to a copending patent application Ser. No. 08/210,356, filed Mar. 18, 1994, entitled "Optical Gain Medium Having Doped Nanocrystals of Semiconductors and Also Optical Scatterers", by Nabil M. Lawandy, now U.S. Pat. No. 5,434,878, issued Jul. 18, 1995.

FIELD OF THE INVENTION

This invention relates generally to sources of electromagnetic energy and, in particular, the invention relates to highly monochromatic sources (narrow spectral linewidth).

BACKGROUND OF THE INVENTION

In a publication entitled "Generation of light by a scattering medium with negative resonance absorption", Sov. Phys. JETP, Vol. 26, No. 4, April 1968 (pps. 835–839), V.S. Letokhov presents a theoretical analysis of the generation of light by a scattering medium with negative resonance absorption or gain. This analysis requires that a photon mean free path ($\Lambda_s$) be much smaller than all of the dimensions (R) of the active scattering region (equation 1). In a discussion of a condition for a generation threshold, an example is provided for an optically excited spherical distribution of ruby particles. ($\lambda = 7 \times 10^{-5}$ cm) with radius $2 \times 10^4$ cm, and the resulting critical radius of the region is shown to be approximately 4 mm. Letokhov also provides a theoretical analysis of scattering particles that are distributed in a gaseous medium with negative absorption, such as a He—Ne or He—Xe gas mixture excited by an electric discharge. The scattering particles are said to effect a non-resonant feedback, while the gaseous active medium effects resonant amplification. The critical effective radius for such a gaseous medium is said to be approximately 1.8 cm. A continuous narrowing of the emission spectrum predicted.

Reference in this regard is also made to an earlier theoretical paper by Letokhov, "Stimulated emission of an ensemble of scattering particles with negative absorption", ZhETF Plasma 5, No. 8, 15 April 1967, (pps. 262–265), wherein the dimensions of the medium are given as $R \gg \Lambda_s \gg \lambda$ where, as before, R is the dimensions of the medium, $\Lambda_s$ is the mean free path of a photon due to scattering, and $\lambda$ is the wavelength of the photon.

Reference is also made to a publication by Ambartsumyan R. V., Basov N. G., Kryukov P. G. & Letokhov V. S. in Progress in Quantum Electronics (ed. Sanders J. H. & Stevens K. W. H.) 109–185 (Pergamon Press, Oxford, 1970), where a theoretical presentation is made at pages 152–153 of a case when the free path of a photon due to scattering, $\Lambda_s \sim 1/Q_s N_0$, the average dimension of the region occupied by a cloud, R, and the wavelength of the emission $\lambda$ satisfy the relation $$R > \Lambda_s > \lambda,$$

and where the mean distance between the scattering particles is much greater than the wavelength.

One problem that is apparent in the approach of Letokhov is that all of the dimensions of the medium must be much greater than the scattering length. By example, each dimension of the medium may be required to be on the order of a centimeter. These dimensional requirements would preclude the use of the medium for many valuable high spatial resolution applications.

By example, one particularly valuable application which could not be achieved in accordance with the teachings of Letokhov is the formation of a thin layer, coating, or body that included the gain medium. Another example is a sphere or cylinder whose radius was comparable to or smaller than the scattering length.

A further problem is the requirement of providing scattering particles in a gaseous medium, particularly one that is excited by an electrical discharge. This may be difficult to achieve in practice, and may be impractical for most applications.

Reference is also made to an article entitled "Generation of stimulated noncoherent radiation in light-scattering media exhibiting chemical reactions", Sov. J. Quantum Electron. 12(5), May 1982, (pps. 588–594), wherein I. A. Izmailov et al. propose that a feedback resulting from scattering be used to achieve lasing in a disperse reactive medium. The feasibility of chemically pumping the laser is estimated on the basis of calculations of the heterophase burning of a drop of fuel in an oxidizing atmosphere. The reactions between NO and $O_3$, Ba and $S_2Cl_2$, and Ba and $N_2O$ are specifically calculated.

A laser device based on this approach, if at all possible to realize in a practical sense, would appear to be limited to a narrow range of specialized applications.

Reference is also made to the following three U.S. Patents, all of which disclose and claim inventions that were made by the inventor of the invention disclosed in this patent application: U.S. Pat. No. 5,157,674, issued Oct. 20, 1992, entitled "Second Harmonic Generation and Self Frequency Doubling Laser Materials Comprised of Bulk Germanosilicate and Aluminosilicate Glasses"; U.S. Pat. No. 5,233,621, issued Aug. 3, 1993, which is a division of the previous patent; and U.S. Pat. No. 5,253,258, issued Oct. 12, 1993, entitled "Optically Encoded Phase Matched Second Harmonic Generation Device and Self Frequency Doubling Laser Material Using Semiconductor Microcrystallite Doped Glasses".

SUMMARY OF THE INVENTION

The foregoing and other problems are overcome by a gain medium which, in accordance with a first aspect of this invention, is a multi-phase system wherein: a first phase is an electromagnetic radiation emitting and amplifying phase; a second phase is an electromagnetic radiation scattering phase; and a third phase is a transparent matrix phase. By example, the emission phase may consist of dye molecules, the scattering phase may consist of $Al_2O_3$ particles, and the matrix phase may consist of a solvent such as methanol. In some embodiments of this invention the emission and scattering phases may be the same phase, as when semiconductor particles are employed. A smallest dimension of a body comprised of the gain medium may be less than a scattering length associated with the scattering phase.

In a further embodiment of this invention, the matrix phase has gain, for example the polymer PPV, and the particles are added for scattering purposes.

In one specific embodiment of this invention laser-like activity is generated in a laser excited methanol solution containing a dye, for example rhodamine, and high index contrast nanoparticles, such as $TiO_2$ or $Al_2O_3$. This gain medium exhibits many of the properties of an efficient laser source, and has a nearly thresholdless input-output behavior. A laser-like activity is intended to encompass a condition wherein a well defined excitation causes the output linewidth of the emission to be narrowed.

Significantly, the dimensional restrictions inherent in the prior art are overcome. It is shown that the laser-like activity occurs when the gain medium has a dimension that is only slightly larger than, equal to, or even less than the scattering length of photons in the medium. This is in sharp contrast to the dimensional requirements predicted by Letokhov et al., as described previously.

In an embodiment of the invention nearly thresholdless laser-like behavior is achieved in a strongly scattering optically pumped dye-methanol solution containing colloidal $TiO_2$ or $Al_2O_3$ nanoparticles. The emission from the optically pumped high gain colloidal medium is shown to exhibit a slope change in its linear input-output characteristics above a critical pump pulse energy. The change in slope is accompanied by a significant narrowing of the output spectral linewidth, with a bichromatic spectrum appearing at high pump energies with some dyes. Excitation of the colloidal medium with 80 picosecond pulses at 532 nm was found to result in an emission which was shorter than a 300 picosecond time resolution of an optical detection system, thus substantiating the occurrence of laser-like behavior and not mere fluorescent behavior.

BRIEF DESCRIPTION OF THE DRAWING

The above described aspects of this invention are made more apparent and are more fully described in the following Detailed Description of the Invention, which is intended to be read in conjunction with the Figures of the attached Drawing, wherein:

FIGS. 6a–6c show the response of the dye solution of FIG. 1, trace "a", (FIG. 6a) and the $TiO_2$/dye solution of FIG. 1, trace "b", to a train of 80 picosecond long pulses, wherein FIG. 6a shows the response of the pure dye at the highest pump energy, whereas FIGS. 6b and 6c show the response of the $TiO_2$ nanoparticle ($2.8 \times 10^{10}/cm^3$) colloidal dye solution at low ($1.2 \times 10^{-2}$ mJ/pulse) and high ($1.2 \times 10^{-1}$ mJ/pulse) pump energies, respectively.

FIGS. 13a–13f each illustrate an embodiment of this invention wherein the medium is contained within a portion of an optical fiber or catheter for providing a desired wavelength at a localized region.

FIG. 21 depicts a particle that includes the gain medium being accelerated due to a force exerted by an input pump beam.

FIG. 22 is a cross-sectional view, not to scale, of a polymer-based, electrically powered light emitting device that benefits from the emission broadening and shifting that is made possible by this invention.

FIG. 23 is a cross-sectional view, not to scale, of a laser diode embodiment of this invention, wherein the gain medium is applied as a coating to an emission face of the laser diode to provide a laser-like emission at a wavelength that differs from the fundamental emission wavelength of the laser diode.

FIG. 24a is an elevation view, not to scale, and FIG. 24b is a top view, not to scale, showing an embodiment of this invention wherein the gain medium of this invention is employed in pumping a second gain medium, such as a dye solution or a laser rod, so as to tune a pump wavelength to the second gain medium.

DETAILED DESCRIPTION OF THE INVENTION

In order to describe in detail a number of novel embodiments of this invention, a description is first made of experimental results which clearly illustrate the novel properties of an embodiment of the medium of this invention.

Experimental Description

Experiments were performed on solutions containing a $1 \times 10^{-3}$ M to $2.5 \times 10^{-3}$ M concentration of rhodamine 640 dye in methanol with varying amounts of either $TiO_2$ (rutile) or $Al_2O_3$ ($\alpha$- phase) nanoparticles. The $TiO_2$ particles had a mean diameter of 250 nm and the $Al_2O_3$ particles were either 280 nm or 33 nm in diameter. The $TiO_2$ particles were coated with a layer of $Al_2O_3$ to prevent flocculation.

Based on the particle sizes and densities, it was determined that these colloids should exhibit sedimentation times of 14.2 hours, 6.6 hours and 882 hours over a 1 cm length, respectively. These times were considerably longer than the approximately 30 minute to 1 hour experiment times.

In addition, the total surface area available for adsorption of the dye molecules to the nanoparticles was determined. Specifically, it was found that the $TiO_2$ particles had a 13.4 $m^2$/gram available surface area for accommodating dye molecules. This value indicates that at a particle density $\rho \sim 10^{10}/cm^3$, approximately 1 % of the dye molecules of a $2.5 \times 10_{-3}$ M dye solution can be accommodated on the nanoparticle surfaces. This upper limit effectively eliminates the possibility that surface effects play a significant role in the observed laser-like properties of the colloidal solution.

The optical scattering properties of the nanoparticles were in the Mie regime. The scattering cross-sections at the peak dye emission wavelength of ~617 nm were computed using the full Mie solutions and found to be far too small to exhibit any morphological resonances. This is believed to be primarily due to the small size parameter, x=ka, where k is the emission wave vector in methanol and a is the particle radius. Using refractive index values of 2.62, 1.77 and 1.33 for $TiO_2$, $Al_2O_3$ and methanol, scattering cross-section values of $1.86 \times 10^{-9}$ $cm^2$, $1.13 \times 10^9$ $cm^2$ and $1.0 \times 10^{-13}$ $cm^2$ were determined for the $TiO_2$ and the two sizes of $Al_2O_3$ particles, respectively.

Figure 7:
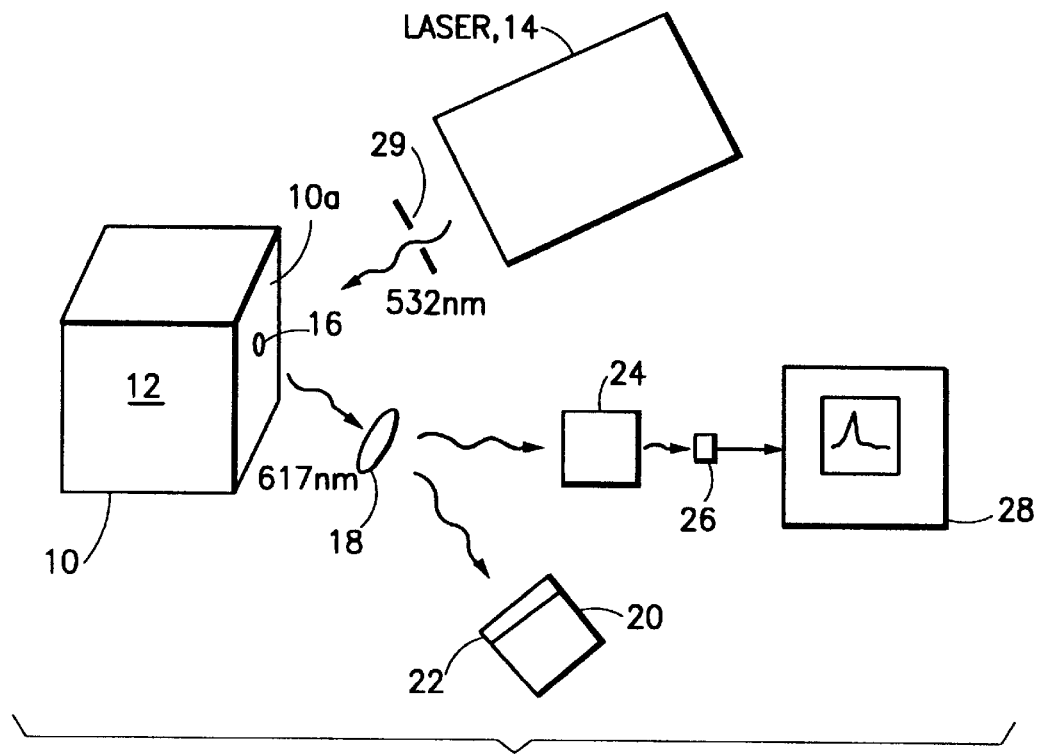
FIG. 7 is a simplified diagram of a system that includes a mechanism that provides laser-like behavior, and from which the data shown in FIGS. 1–6 was generated.

As depicted in FIG. 7, a transparent (at the wavelengths of interest) cell 10 contained a solution 12 having nanoparticle methanol colloids impregnated with rhodamine 640 perchlorate at concentrations in the 10–3 M range. The cell 10 had nominal dimensions of 1 cm×1 cm×1 cm.

It should be noted that these cell dimensions were selected for convenience in conducting the experiments. That is, and as will be described below, these cell dimensions are not to be construed as a limitation upon the practice of this invention.

The solution 12 was optically pumped off-axis by linearly polarized 532 nm radiation from a frequency doubled Nd:YAG laser 14 operating at 1.064 mm. Experiments were performed with either a Q-switched laser which produced single 7 nanosecond pulses, or with a Q-switched and mode-locked laser which produced a 125 nanosecond long train containing nine 80 picosecond long pulses. The 532 nm radiation was found to have a 50$\mu$m small signal penetration depth into a $2.5 \times 10_{-3}$ M solution of pure dye in methanol, making it smaller than the shortest optical scattering lengths (ls) used in any of the experiments. The area of the laser spot 16 at the incident face 10a of the cell 10 was measured to be $2.5 \times 10^{-2}$ $cm^2$ for the 7 nanosecond pulses, and $7.85 \times 10_{-3}$ $cm^2$ for the 80 picosecond excitation. The measurements using the long pulses were performed at a repetition rate of 5 Hz, while the 80 picosecond pulse measurements were performed at a Q-switch rate of 25 Hz.

These low repetition rates were used to avoid any dye degradation effects, and are not a limitation upon the practice of the invention. The maximum energy per pulse for the experiments were approximately 10 mJ and 0.12 mJ for the long and short pulses, respectively. The output from the face 10a of the cell 10 was collected using a lens 18 and was sent to an optical multichannel analyzer 20 with a liquid nitrogen cooled CCD array 22, as well as through a monochromator 24 to a fast photodiode 26 and oscilloscope 28 having a 300 picosecond overall time resolution.

Example

A first series of experiments were performed using 7 nanosecond long pulses pumping a $2.5 \times 10_{-3}$ M rhodamine 640 perchlorate in methanol solution in the cell 10. The excitation of the pure dye solution resulted in the spectrum shown in FIG. 1, trace "a". This spectrum exhibited a main peak at 610 nm with a shoulder at 640 nm. This spectrum was found to remain constant for the entire range of pump pulse energies up to 10 mJ. The wavelength integrated fluorescence as a function of pump energy exhibited a saturation behavior with a saturation energy of 0.26 mJ and is shown by the open circles in FIG. 2. This saturation energy along with the spot size and pump pulse duration agrees with the saturation intensity given by $I_s \sim h\nu/\sigma_p\tau_{sp}$=0.7 MW/$cm^2$, where $\sigma_p$ is the pump absorption cross section at 532 nm ($\sigma^p \sim 1.33 \times 10^{-16}$ $cm^2$) and $\tau_{sp}$ is the $S_1 \rightarrow S_0$ spontaneous lifetime (4 nanoseconds).

Figure 1:
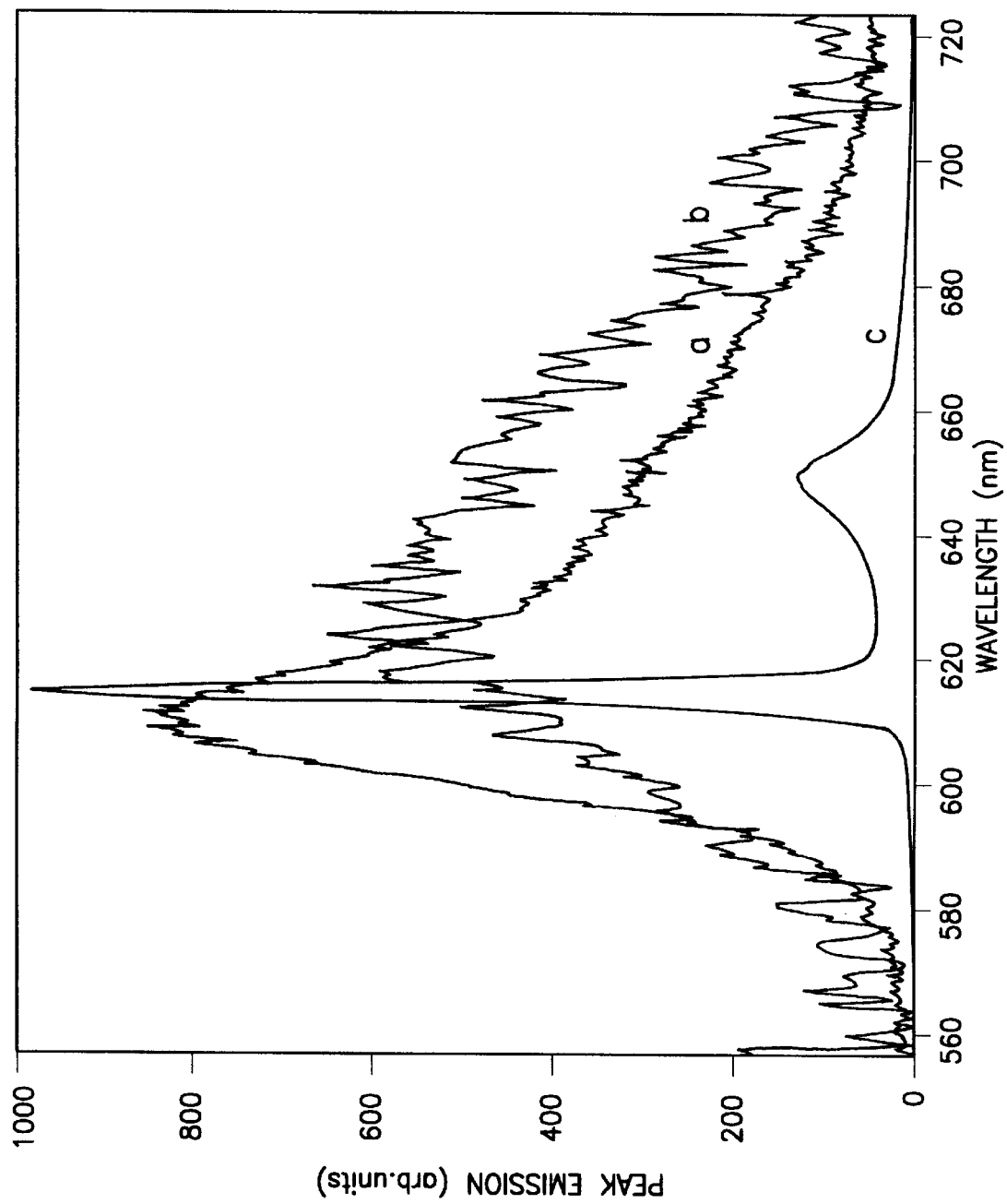
FIG. 1 graphically illustrates three different emission spectrums that were obtained using (trace "a") a pure dye excited by an excitation source; (trace "b") the dye in combination with scattering particles below a threshold excitation; and (trace "c") the dye in combination with scattering particles above the threshold excitation.
Figure 2:
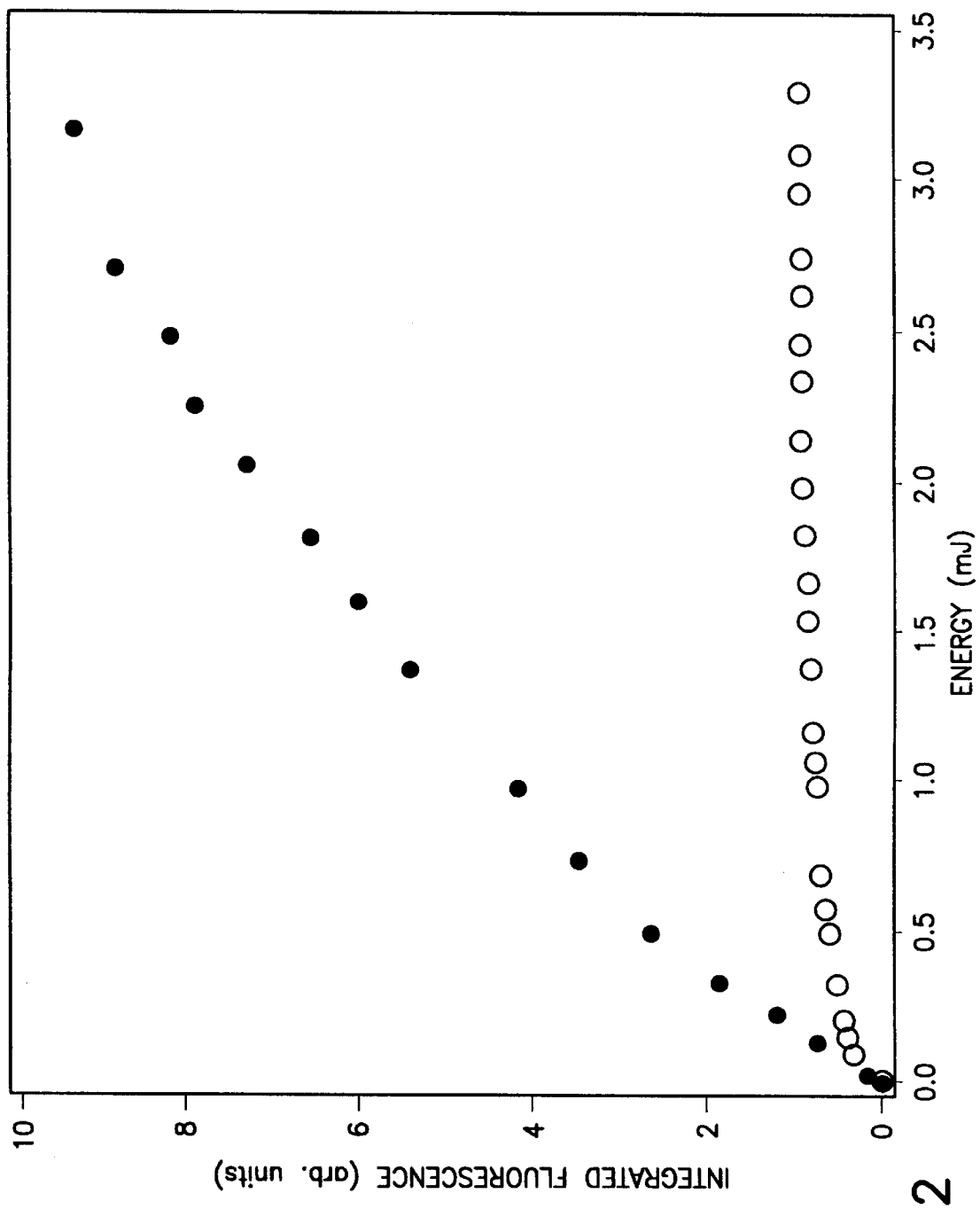
FIG. 2 illustrates a plot of wavelength integrated emission as a function of the pump pulse energy for the pure dye solution of FIG. 1, trace "a", (open circles) and the $TiO_2$ nanoparticle colloidal ($2.8 \times 10^{10}/cm^3$) dye solution of FIG. 1, trace "b", (closed circles).

Similar optical pumping experiments were performed in the methanol-dye solution containing $2.8 \times 10^{10}/cm^3$ of the $TiO_2$ nanoparticles. The results of these experiments were strikingly different. The spectrum at the lowest excitations exhibited a linewidth of 76 nm, as compared to the 36 nm width of the pure dye solution. When the energy of the excitation pulses was increased, the unpolarized emission at $\lambda \sim 617$ nm grew rapidly and narrowed as shown in FIG. 1, trace "b". As the pump energy was increased even further, a bichromatic spectrum was observed. This bichromatic spectrum was found to be similar to that reported in strongly driven ring dye lasers. The 640 nm emission was only observed in cells thicker than 100 $\mu$m, and is associated with stimulated emission on a weaker vibrionic transition. The solid circle data in FIG. 2 shows the wavelength integrated emission as a function of pump energy.

It is important to note that the colloidal solution containing the $TiO_2$ nanoparticles does not exhibit the strong saturation behavior observed in the pure dye solution. That is, the use of the medium of this invention provides a non-saturable source of highly monochromatic optical energy.

Figure 3:
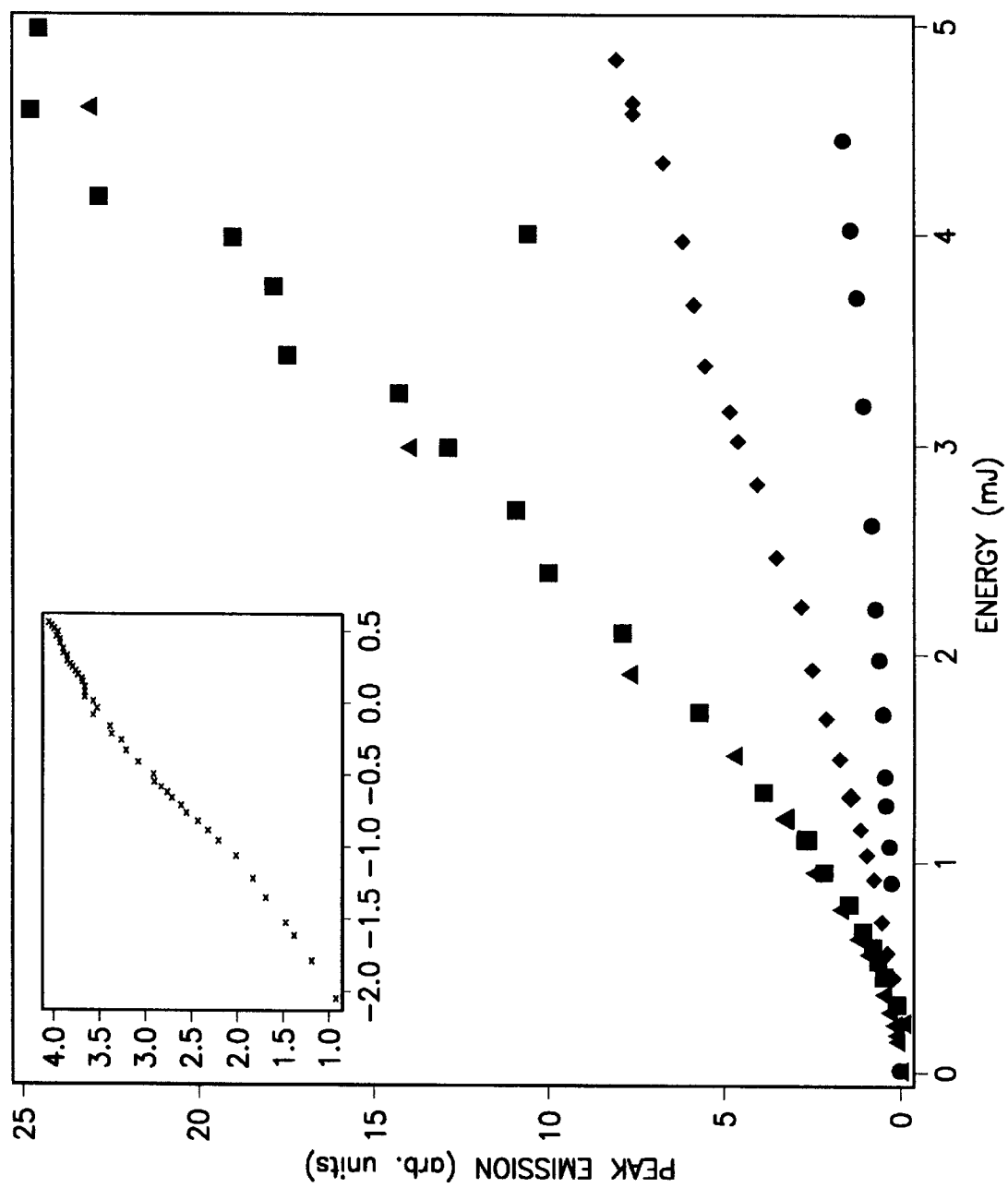
FIG. 3 illustrates a peak emission as a function of the pump pulse energy for four different $TiO_2$ nanoparticle densities. specifically, nanoparticle densities of $1.4 \times 10^9/cm^3$, $7.2 \ 10^9/cm^3$, $2.8 \times 10^{10}/cm^3$ and $8.6 \times 10^{11}/cm^3$ are shown by solid circles, diamonds, squares and triangles, respectively. The inset shows the data on a logarithmic scale for a nanoparticle density of $2.8 \times 10^{10}/cm^3$.

It is also important to note the dependence of the λ~617 nm peak emission on pump energy for various nanoparticle densities that is shown in FIG. 3. More specifically, FIG. 3 shows a well defined threshold for the change in slope efficiency at 617 nm for all of the particle concentrations. When this data is plotted on a logarithmic scale, the result is the characteristic S-shaped curve for laser behavior shown in the inset of FIG. 3. The curve exhibits a very gentle curvature characteristic of nearly thresholdless laser behaviors, which approaches a straight line when all of the spontaneous emission modes are capable of lasing. Analysis of this line shape data reveals that at the same pump energy where a change in slope in the input/output behaviors is observed, the emission linewidth collapses rapidly to 4 nm.

Figure 4A:
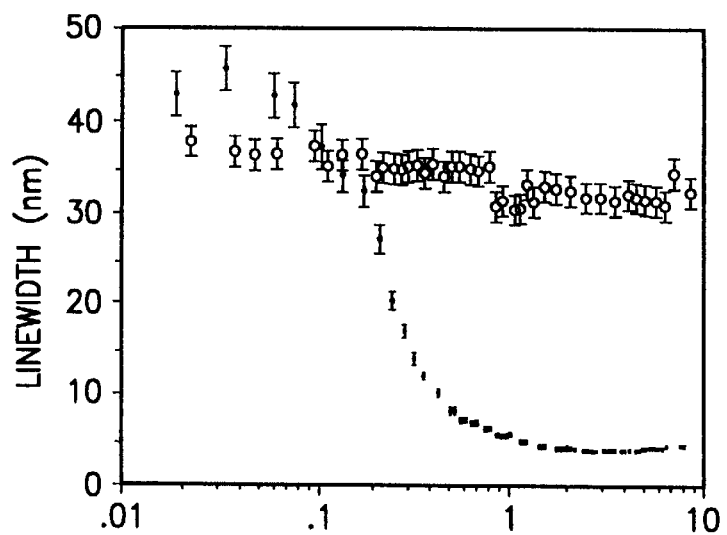
FIGS. 4a–4c illustrate an emission linewidth as a function of the pump pulse energy for three different $TiO_2$ nanoparticle densities. More specifically, FIGS. 4a–4c correspond to densities of $5.7 \times 10^9/cm^3$ (solid circles), $2.8 \times 10^{10}/cm^3$, and $1.4 \times 10^{11}/cm^3$, respectively. The open circles in FIG. 4a represent the emission linewidth of the pure dye solution of FIG. 1, trace "a", as a function of the pump pulse energy.
Figure 4B:
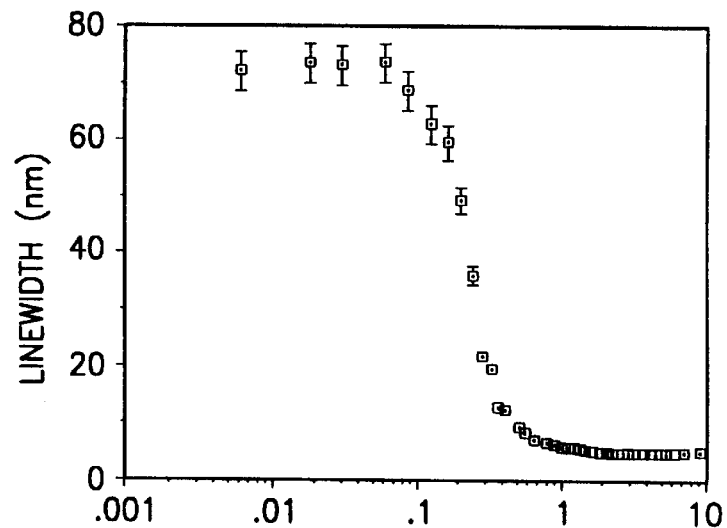
Figure 4C:
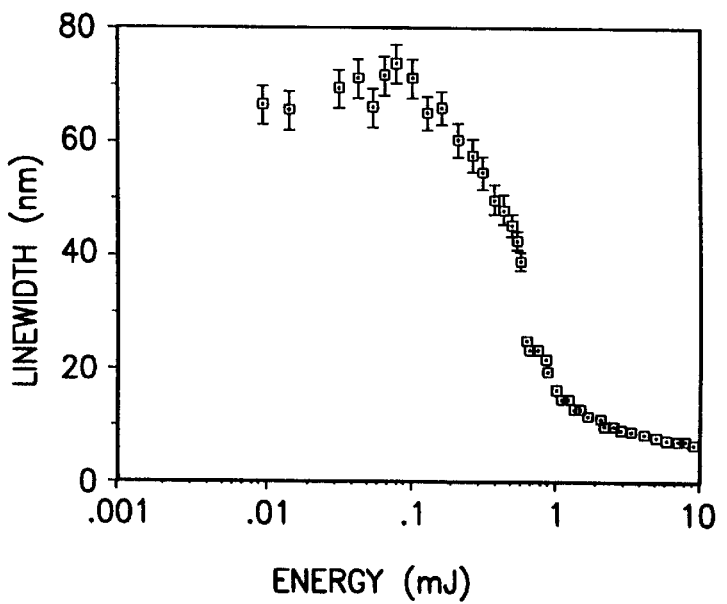

FIGS. 4a–4c show plots of the full width at half maximum of the emission as a function of the pump pulse energy for three different $TiO_2$ nanoparticle concentrations. FIG. 4a also shows the linewidth of the pure dye as a reference (shown in open circles). The results plotted in FIG. 4 clearly show the quasi-steady state laser behavior that is taking place in the medium 12.

It is important to note that this quasi-steady state laser behavior occurs in an optically pumped solution that is not located within a resonant cavity structure, as is the case for a conventional dye laser system.

The data collected on various nanoparticle concentrations was employed to determine the relative dependence of the slope efficiency, ζ, of the laser on the nanoparticle concentration. The results revealed a linear dependence of ζ on ρ until a critical value $\rho_c = 5\times10^{10}/cm^3$, where increasing the particle density produced no appreciable increase in the slope efficiency for the emitted light output at λ~617 nm. Similar results were observed with the other two particle sizes at densities which corresponded to comparable scattering mean free paths. In addition, it was found that the scattering efficiency was also independent of the dye concentration over the range of $1\times10^{-3}$ M to $5\times10^{-3}$ M.

Figure 5:
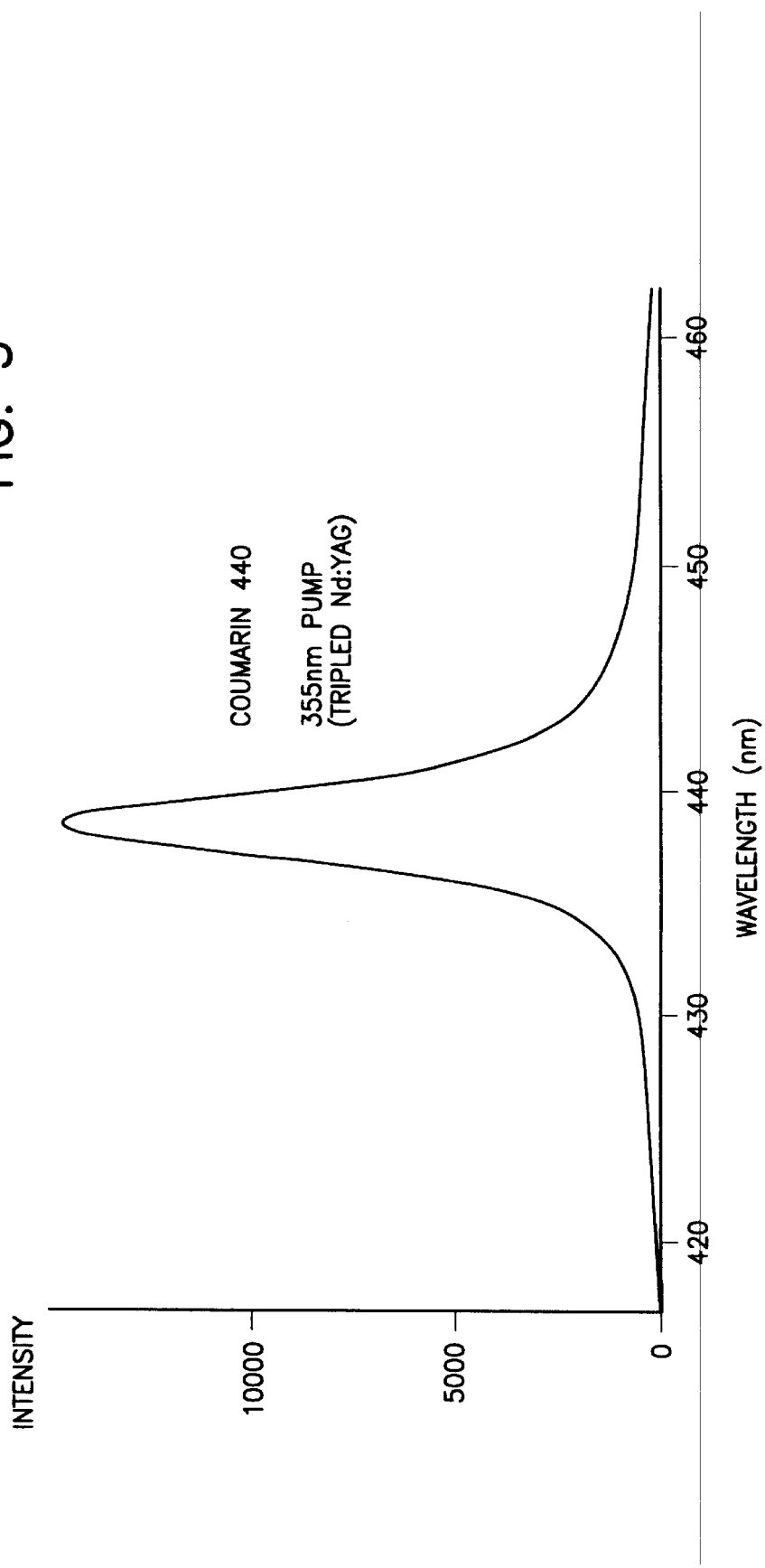
FIG. 5 is a graph that plots intensity versus wavelength for a gain medium comprised of coumarin 440 and scattering particles.

In a further set of experiments the light emitted from the cell 10 was sent through the monochromator 24 to the fast photodiode 26 and oscilloscope 28 in order to determine the temporal characteristics of the emission at different wavelengths. FIGS. 5a–5c show the traces recorded for 3 mJ per pulse excitation (7 nanosecond long) of the pure dye, the intense 617 nm emission, and the 640 nm emission peak. These results indicated that the pure dye and the 640 nm emission both peak after the pump pulse, while the 617 nm radiation reaches a maximum before the peak of the pump pulse.

Figure 6A:
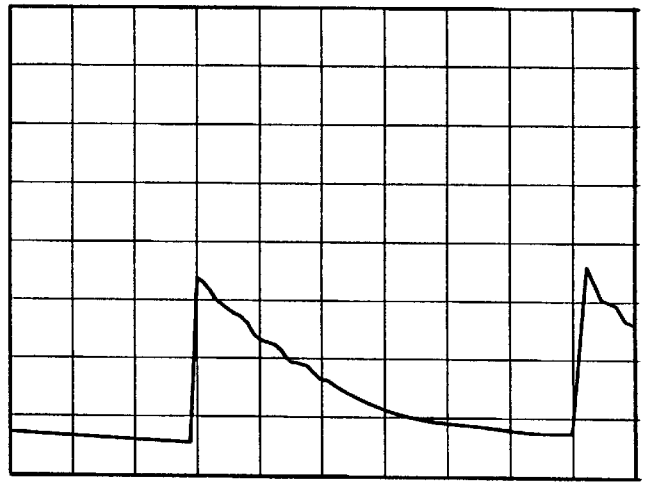
Figure 6B:
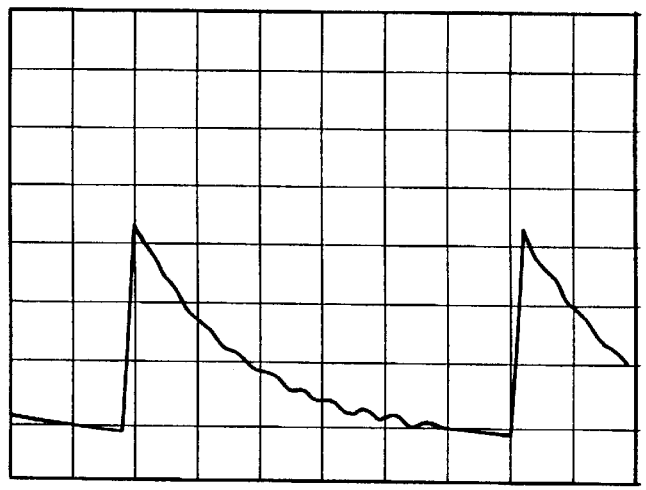
Figure 6C:
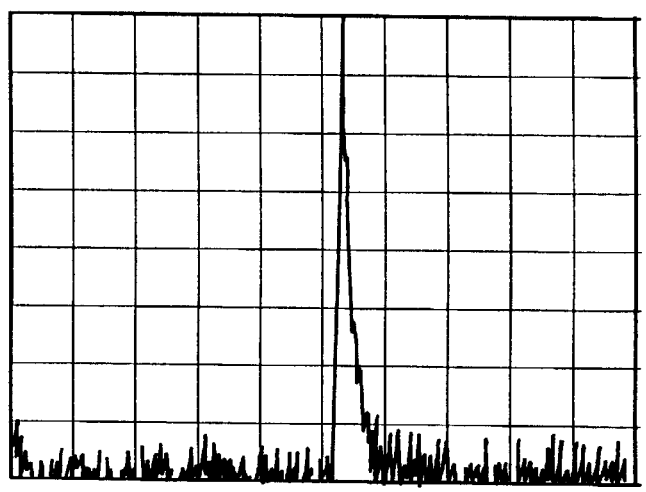

Excitation with a train of 80 picoseconds pulses also revealed a threshold behavior in the temporal characteristics of the colloidal dye/methanol/nanoparticle solution 12. When the pump pulse energy was below that required for the onset of laser action, the peak emission at 614 nm exhibited a long 4 nanosecond decay at all pump energies that was identical to that observed in the pure dye solution. In addition, a large background signal was observed since the pulses arrived every 13.15 nanoseconds, a pulse repetition rate which barely allowed the excitation to relax. However, when the pump pulse energy was increased beyond the threshold point a sharp spike appeared which was found to be shorter in duration than the 300 picosecond resolution of the oscilloscope 28. A further increase in energy resulted in only the sharp spike, and in a nearly complete recovery between pulses in the mode locked and Q-switched train. These results are shown in the oscilloscope traces of FIG. 6.

The data that is presented above with reference to FIGS. 1–6 clearly shows that laser or laser-like activity is occurring in the medium 12. This can be stated because of: (a) the observed change in slope at a well-defined pump energy; (b) the linear input-output behavior both below and above threshold; (c) the spectral line narrowing above a well-defined pump energy; and (d) the temporal compression above a threshold excitation. The comparison of this data to the results obtained for the pure dye mixture reinforces the determination of laser action.

Figure 8A:
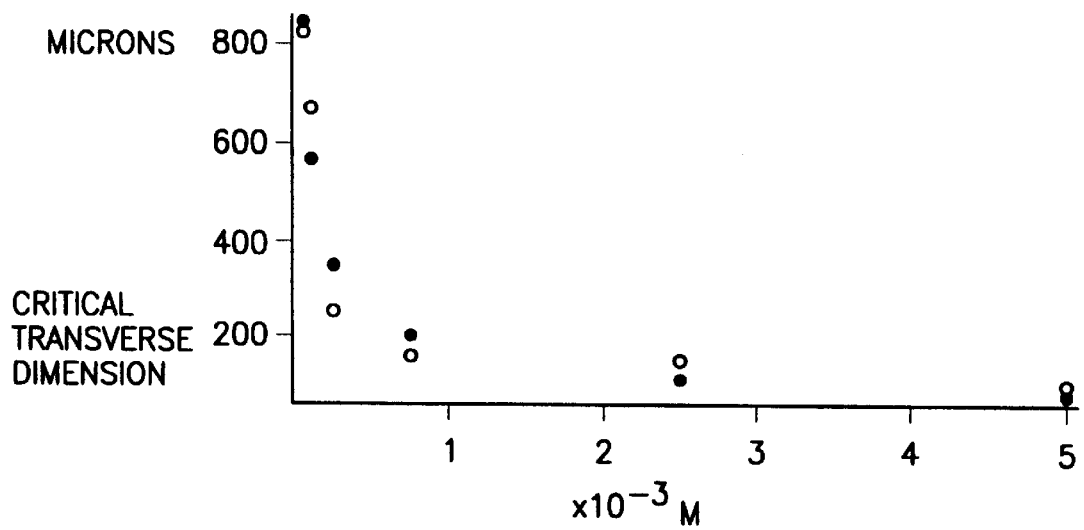
FIG. 8a is a plot of critical transverse aperture dimension as a function of dye concentration.
Figure 8B:
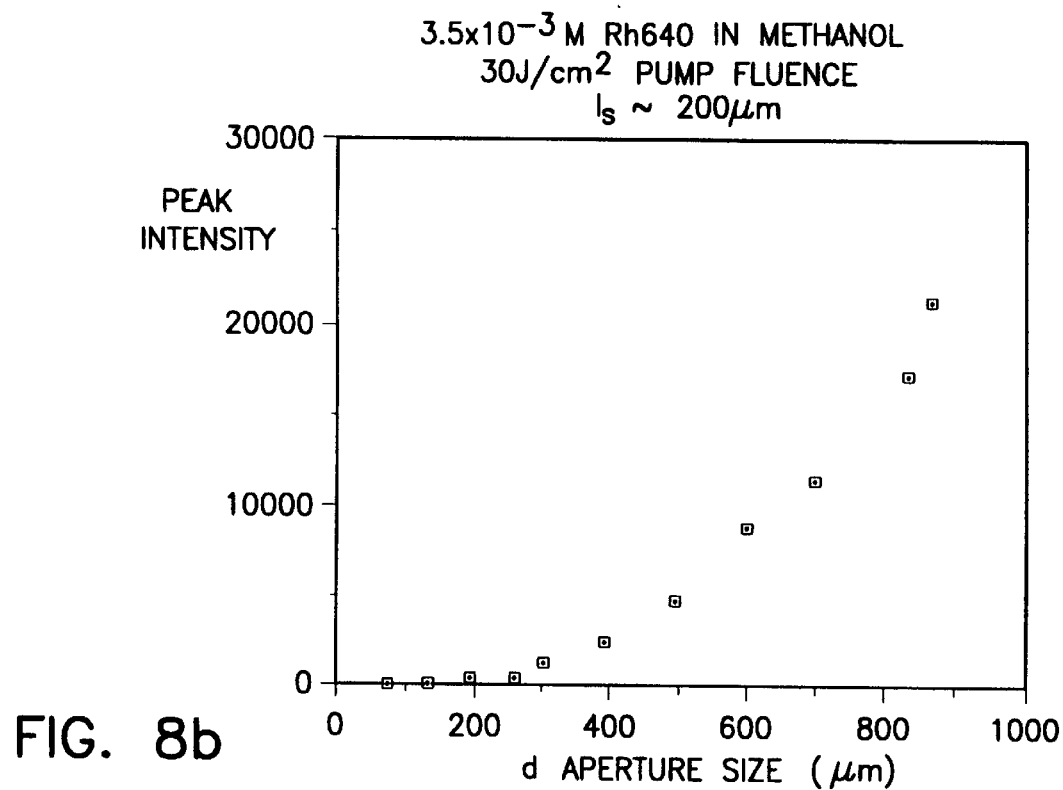
FIG. 8b is a plot of peak intensity versus aperture size (microns) for a gain medium having a $3.5 \times 10_{-3}$ M dye concentration.
Figure 8C:
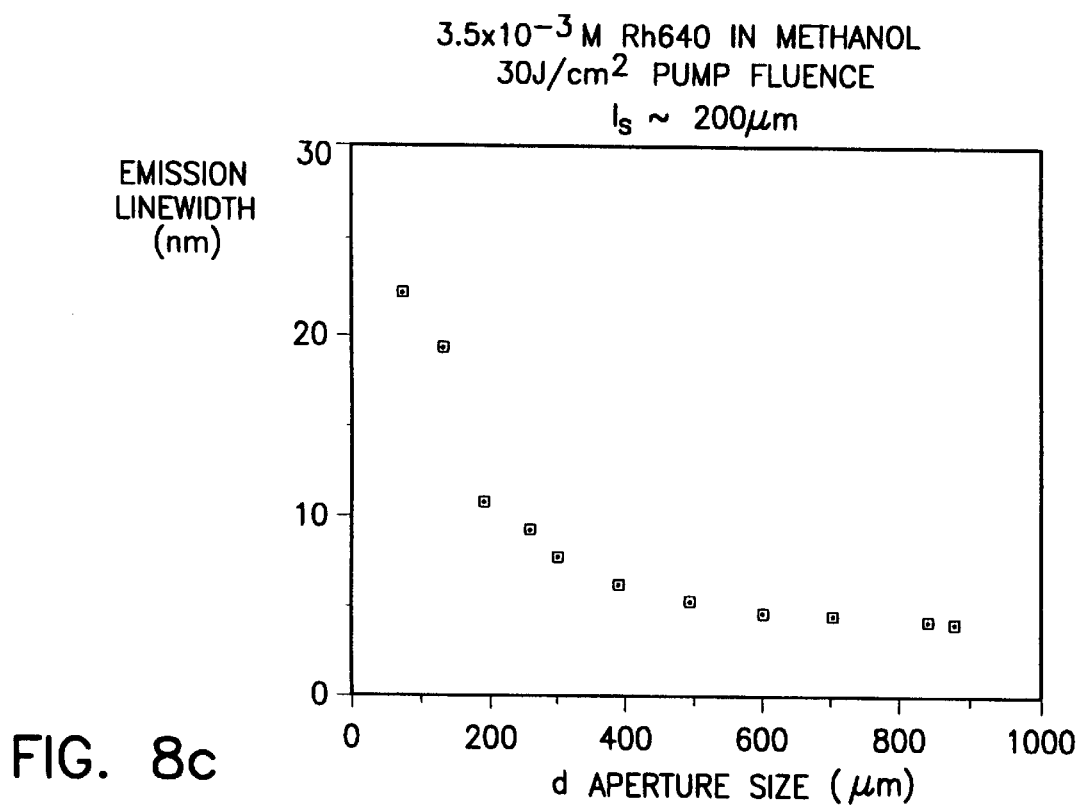
FIG. 8c is a plot of emission linewidth (nanometers) versus aperture size (microns) for the gain medium having a $3.5 \times 10_{-3}$ M dye concentration.
Figure 8D:
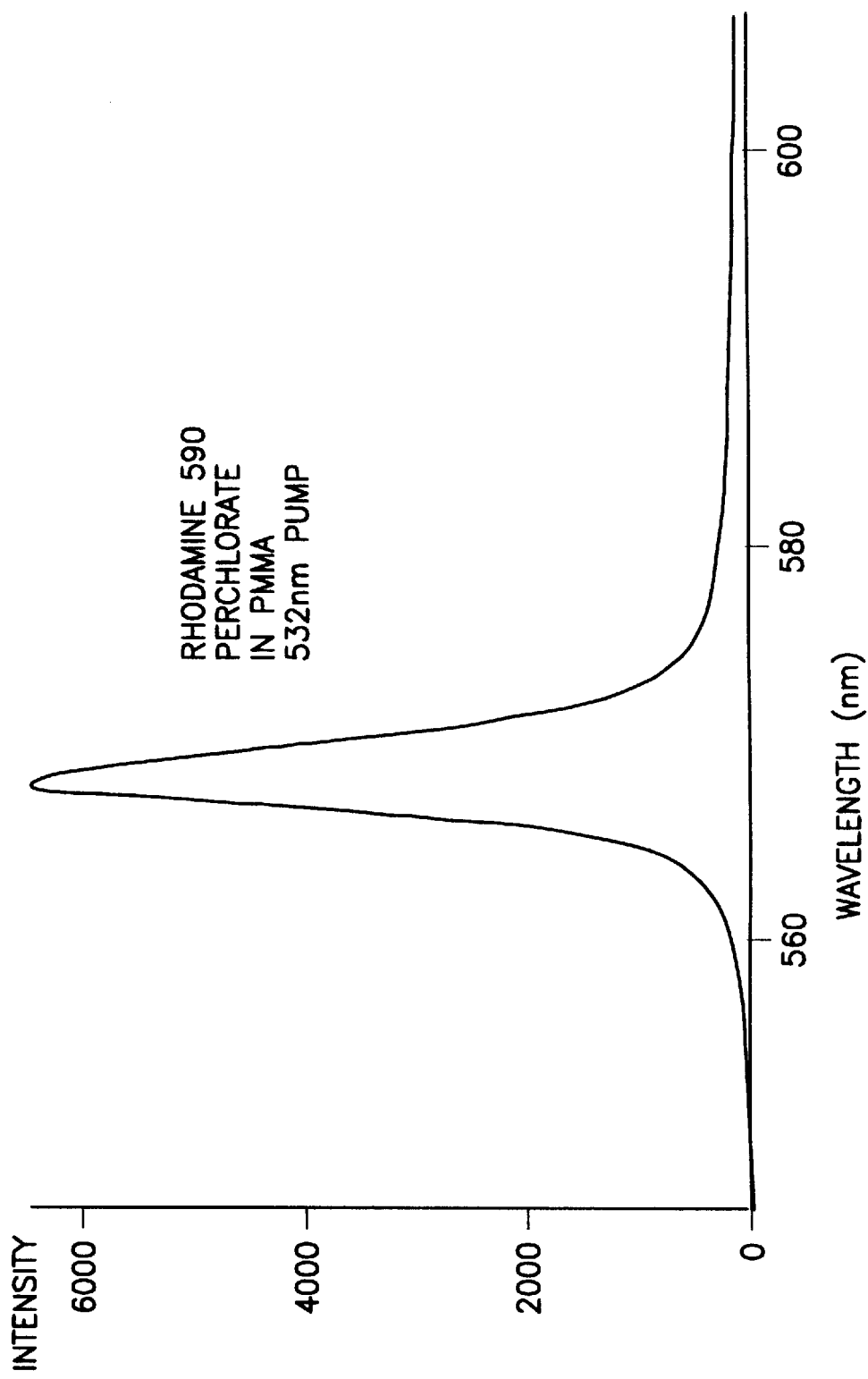
FIG. 8d plots emission intensity versus wavelength for a thin (0.5 mm thick) monolithic solid sample of the gain medium.

FIG. 8a is plot of critical transverse aperture dimension as a function of dye concentration; FIG. 8b is a plot of peak intensity versus aperture size (microns) for a gain medium having a $3.5\times10^{-3}$ M dye concentration; FIG. 8c is a plot of emission linewidth (nanometers) versus aperture size (microns) for the gain medium having a $3.5\times10^{-3}$ M dye concentration; and FIG. 8d plots emission intensity versus wavelength for a thin (0.5 mm thick) monolithic solid sample of the gain medium.

It can be seen that an emission from the gain medium 12 is possible over a region having at least one dimension (aperture size or transverse dimension) that is less than or of the order of the associated scattering length of the medium 12. This is an important aspect of this invention, in that it makes possible a wide range of applications wherein it is desirable to provide the medium 12 within a small volume, or as a thin coating or layer.

The following analysis is presented in order to aid in a qualitative understanding of this invention. While there is no intent to limit the scope of this invention by the theory now to be presented, this theory is believed to be accurate and consistent with observable facts and accepted scientific principles.

The explanation for the observed laser-like behavior of the optically pumped colloidal gain medium is, at present, not totally understood. At first glance one is tempted to think in terms of photon diffusion as providing a kind of non-resonant feedback for the high gain laser dye. One of the main problems with invoking the light diffusion process as the origin of the pseudo-cavity made evident in the experiments detailed above is that the effect requires that the smallest dimension of the scattering medium be large compared to the optical scattering length. However, in the case of the experiments detailed above the scattering length at the lasing wavelength was typically of the order of 200 µm, requiring that every dimension of the sample be of the order of several millimeters in order that the diffusion time of photons is a meaningful concept. As was described above in relation to FIGS. 8a–8d, the laser-like behavior was observed in samples which were 100 µm thick. In a further series of experiments it was found that the linewidth collapse could be observed at cell thicknesses as small as 30 µm, or one-sixth the scattering length. These results suggest that the diffusive-type model predicted by Letokhov, in its simplest form, is inadequate for explaining the observed laser-like activity in the gain medium 12. Experiments with samples which have every dimension smaller than a scattering length, and which are index of refraction matched at the boundaries, also exhibit the laser-like behavior.

The collapse of the linewidth within a region having a dimension that is less than the scattering length of the medium 12 is believed may be due to a previously unobserved or unrecognized type of radiative decay of a dye molecule population. conventionally, a population of dye molecules exhibits an incoherent decay, wherein the total power of the emitted radiation is the sum of the powers of each dye molecule, or Power=$\Sigma A_i^2$. The effect observed in the medium 12 of this invention instead appears to exhibit the operation of a coherent decay mechanism wherein the emitted power is instead given by $(\Sigma A_i)^2$. By example, for a conventional, two dye molecule system the total emitted power would be 2, whereas for the medium 12 of this invention the total emitted power is 4.

The result is an emission from a region, having a smallest dimension of only some hundreds of micrometers or less, of substantially monochromatic light having a high intensity or brightness.

Having thus described the physical and optical characteristics of the medium 12 of this invention, a description will now be provided of a number of exemplary embodiments of this invention that employ the medium 12. In some of these embodiments the medium 12 is provided as a coating or layer, similar to a paint or a cream. For certain of these embodiments the dye molecules and scattering particles are supplied in conjunction with a suitably transparent (at the wavelengths of interest) binder or matrix material, such as a polymer. That is, the dye molecules and scattering particles are immobilized within the matrix. Also, in the ensuing description it should be realized that the teaching of this invention is not limited to use only with dye molecules. For example, the invention can also be practiced with small particles of a semiconductor (such as CdSe) of a type suitable for emitting light in response to input optical or electrical energy. In this embodiment the semiconductor particles can be used with the scattering particles described above, or may serve themselves as scattering particles. In a further embodiment of this invention the gain material and matrix are one and the same, and have scattering particles dispersed throughout. For example, the gain/matrix material is comprised of the polymer such as polyphenylene vinylene (PPV), and the scattering particles are nanoparticles of $Al_2O_3$ and/or $TiO_2$ that are dispersed with the PPV. Also by example, CdSe particles can be provided in the polymer PMMA, or particles of PPV can be provided in PMMA.

Figure 9A:
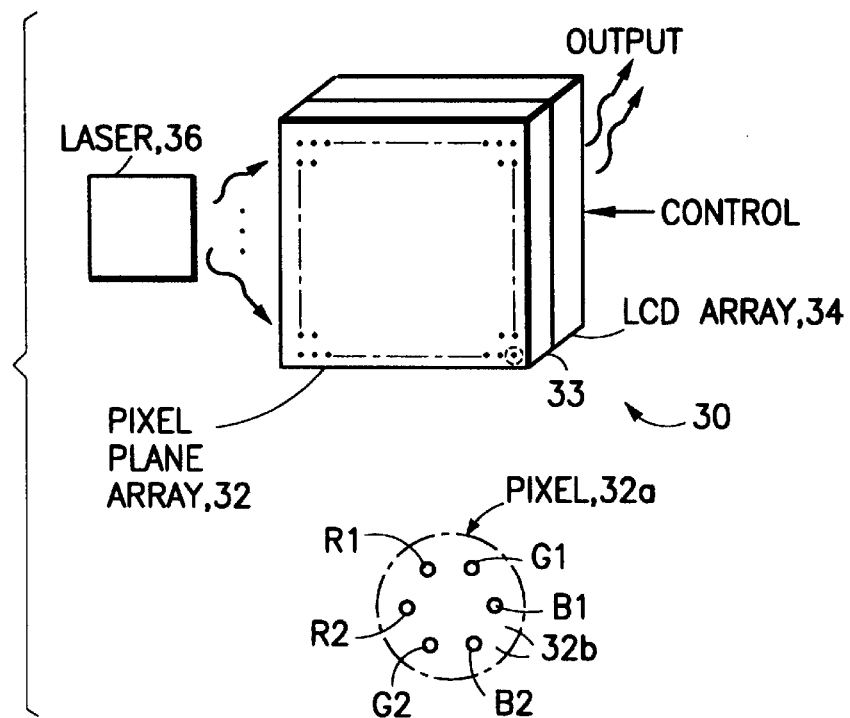
FIGS. 9a and 9b each illustrate an embodiment of this invention wherein the medium is employed to form a plurality of pixels of a display apparatus, the pixels being scanned during use by a laser.

FIG. 9a illustrates an embodiment of this invention wherein the medium 12 is employed to form a plurality of pixels of a display apparatus, the pixels being scanned during use by a laser. More particularly, a display system 30 includes a pixel plane 32 which comprises a transparent substrate 33 having a plurality of pixels 32a formed on or within a surface thereof. Each pixel 32a may be comprised of a plurality of subpixels 32b each of which is comprised of the medium 12. Each sub-pixel 32b may have dimensions of a hundred micrometers or less. The medium 12 is provided as, by example only, six sub-pixels each containing a different type of dye molecule in combination with scattering particles. In the example shown, two of the regions (R1 and R2) emit wavelengths within the red portion of the spectrum, two of the regions (G1 and G2) emit wavelengths within the green portion of the spectrum, and two of the regions (B1 and B2) emit wavelengths within the blue portion of the spectrum.

In one embodiment an LCD array 34 is positioned adjacent to a surface of the screen or pixel plane 32. The LCD array 34 is controlled by a control signal to selectively permit the emitted radiation from one or more of the sub-pixels 32b to pass through to an observer. A scanning laser 36 is provided to scan the pixel array 32 under the control of a video scan signal. The scanning of the pixel array causes each of the non-saturable sub-pixels 32b of a scanned pixel 32a to emit a narrow band of wavelengths that is determined by the constituent dye molecules. Due to the presence of the scattering particles, the output of a given sub-pixel 32b appears to an observer as a small point of brilliant, substantially monochromatic light. The light is not collimated, owing to the scattering nature of each pixel, and is thus not confined to a narrow range of angles.

Coincidentally with the illumination of the sub-pixels 32b, one or more elements of the LCD array 34 is selectively "opened" to permit the emitted wavelength from one or more of the sub-pixels 32b to pass through to the observer. When the pixel array is scanned at video rates the visual effect is the formation of a brilliant color image without saturation, thereby enabling viewing at a great distance.

It should be realized that more or less than 6 sub-pixels 32b can be employed for a given pixel 32a. The use of 6 sub-pixels enables 2 different shades of each primary color to be generated (for example 620 nm and 640 nm for red), and also a hexagonal sub-pixel pattern to be formed which provides an efficient packing density.

In a further embodiment three sub-pixels are provided, one each for red, green, and blue. In another embodiment two sub-pixels are provided, for example red and green, and the pixels are scanned with a laser that provides the color blue.

The laser 36 can be positioned to illuminate the pixel array from the rear, or can be positioned to illuminate the pixel array from the side, thereby reducing the overall depth of the display.

Figure 9B:
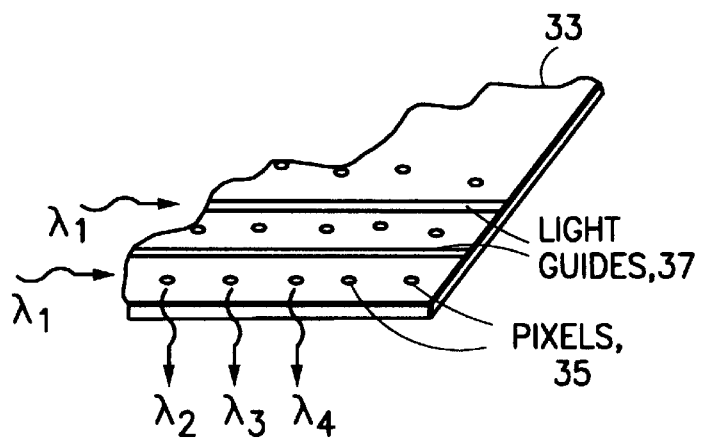

FIG. 9b shows a portion of a substrate 33 having a plurality of pixels 35 disposed on a surface thereof. The pixels 35 can be deposited in a liquid form and subsequently cured or dried. Each pixel is comprised of the optical gain medium of this invention. In the embodiment of FIG. 9b the plurality of light guides 37 are provided on a surface or within a surface of the substrate 33 and are provided with a first wavelength from a laser (not shown) that is disposed along an edge of the substrate. If the light guides 37 are optical fibers leakage of the input wavelength is employed to optically pump the adjacent pixels. If the light guides 37 are instead optical waveguide-type structures, then evanescent coupling of radiation out of the waveguides is employed to optically pump the adjacent pixels.

In a further embodiment of the invention each of the pixels 35 can be coupled to an associated thin film transistor (TFT) which injects, when energized, charge carriers into the pixel. In this embodiment the charge carriers are employed as an excitation source to cause the pixel to emit the desired wavelengths.

In all of these embodiments of a display apparatus the pixels operate so as to be substantially non-saturable and to output electromagnetic radiation within a narrow band of wavelengths. As such, the pixels of this invention are readily distinguishable from conventional phosphor-type pixels that are commonly used in televisions, video monitors and the like.

Figure 10A:
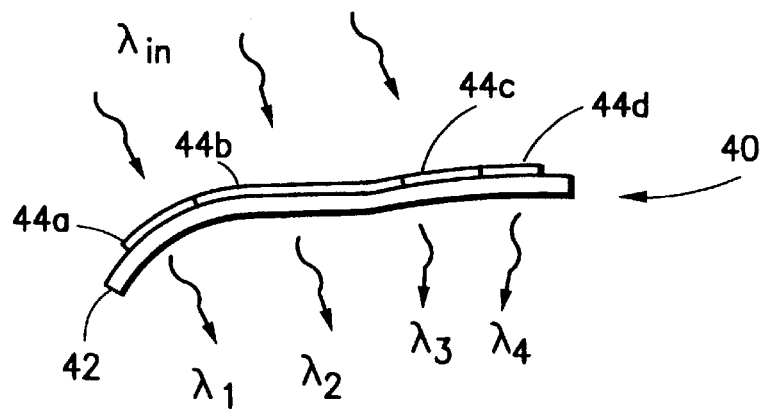
FIG. 10a illustrates an embodiment of this invention wherein the medium is employed to form a plurality of regions upon a surface of a transparent substrate for simultaneously providing a plurality of different output wavelengths in response to an input wavelength.

FIG. 10a illustrates an embodiment of this invention wherein the medium 12 is employed to form a plurality of regions upon a surface of a transparent substrate for simultaneously providing a plurality of different output wavelengths in response to an input wavelength.

Specifically, there is illustrated a cross-sectional view of a structure 40 comprised of a transparent substrate 42 having one or more regions or layers 44a–44d each of which is comprised of the medium 12. Each layer 44a–44d contains dye molecules selected for providing a desired output wavelength ($\lambda_1-\lambda_4$) in response to an input wavelength ($\lambda^{in}$) provided from a suitable laser source (not shown). If the layers 44a–44d are simultaneously illuminated then the plurality of output wavelengths are simultaneously emitted.

One valuable application for the structure 40 is to provide a plurality of different wavelengths to a surface of the skin when removing undesirable skin pigments, such as port wine stain and tattoos. In this case, the layers 44a–44d are formed in the shape of the pigment area to be removed, with each layer containing, by example, a dye molecule or semiconductor particles, selected to emit a wavelength that is strongly absorbed by the underlying pigment.

Preferably, the substrate 42 is made flexible so as to conform to the contours of the body part. The presence of the substrate 42 is optional, although it is useful when it is desired to first deposit the layers 44a–44d in a desired pattern, and also for preventing the contact of the medium 12 with the skin.

It is also within the scope of this invention to employ low angle diffusion so as to mix the emitted wavelength with one another, instead of providing well-defined spatial regions each emitting a specific, very narrow band of wavelengths.

Figure 10B:
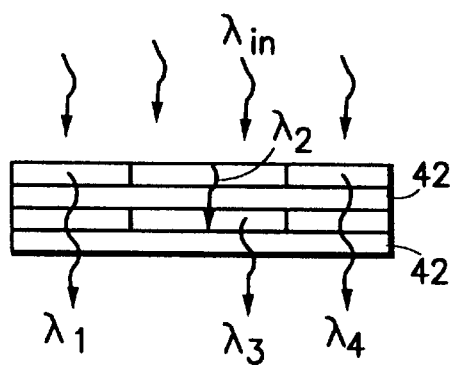
FIG. 10b illustrates a multi-layer configuration of a plurality of gain medium-bearing substrates.

It is also within the scope of this invention to stack two or more gain medium bearing substrates one upon another in a multi-layered configuration. In this case, the wavelengths emitted from upper ones of the substrates may pars unhindered through transparent (at the wavelengths of interest) portions of lower substrates, or a wavelength emitted from an upper substrate may be used to pump a gain medium region on a lower substrate. These two cases are shown generally in FIG. 10b, where $\lambda_1$ and $\lambda_4$ pass through the multi-layered structure, and where $\lambda_2$ is used to optically pump the lower gain medium region to generate $\lambda_3$.

Figure 11:
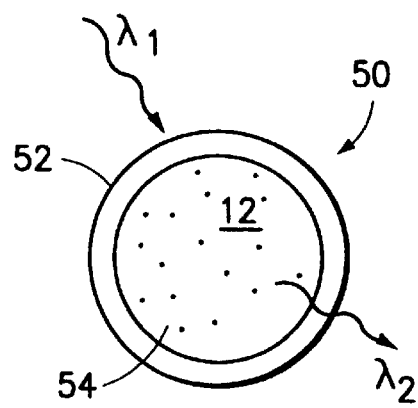
FIG. 11 illustrates an embodiment of this invention wherein the medium is encapsulated within a small sphere.

FIG. 11 illustrates an embodiment of this invention wherein the medium is encapsulated within a small sphere 50. By example, the sphere 50 has a diameter of the critical diameter or layer. The sphere 50 has an outer surface 52 and an inner region 54 which contains the medium 12. In response to illumination with a first wavelength the medium 12 emits the second wavelength as determined by the constituent gain medium in combination with the scattering particles.

In use, a large number of the spheres 50 can be employed for blanketing a surface such as, for example, a surface on or adjacent to a roadway or runway. In response to laser illumination, that portion of the surface having the spheres 50 emits a brilliant and substantially monochromatic light, thereby making a particular portion of the surface readily discernable to the eye or to a suitable detector. In this regard, the medium 12 may contain dye molecules that are responsive to infrared or near-infrared wavelengths which may more readily penetrate fog and rain. One suitable dye for this application is known in the art as IR 144.

It is also within the scope of this invention to suspend the small gain medium bodies within the atmosphere for use as by example, an atmospheric marker for adaptive optics calibration. In this case the small gain medium bodies can be optically pumped by a ground-based or not ground-based laser source.

It is also within the scope of the invention to pump the gain medium with a natural pump source, such as lightening.

It is also within the scope of the invention to pump the gain medium with a flash lamp.

Further in accordance with this embodiment of the invention, the spheres 50 can be poured onto water so as to leave a detectable trail behind a ship. This enables, by example, an aircraft carrier to leave a detectable trail that can be followed by returning aircraft. In this example, each aircraft is equipped with a suitable laser source for illuminating the surface of the water and with a suitable detector, such as an IR imaging array, for detecting the emitted wavelengths. The particular choice of a wavelength for a given day or mission can be selected so as to provide a degree of security. That is, the aircraft expect to detect a specific wavelength, and may be provided with a corresponding filter or detector for the expected wavelength.

Further in this regard, the medium 12 can be employed as a coating dispensed as, by example, an aerosol or a liquid to identify targets for ordinance having a sensor that is responsive to the emitted wavelength. In general, the medium 12 finds use in "friend or foe" detection systems. For example, in a battlefield situation all vehicles are provided with a portion coated with the medium 12 containing dye molecules selected to emit a predetermined wave length. When illuminated by a laser source only those vehicles having the coating will emit the expected wavelength. Any vehicles not emitting a wavelength when illuminated, or not emitting the predetermined wavelength, are suspect.

It can be appreciated that the medium 12 can be provided in a low cost manner as a coating applied directly to an object, or upon a changeable portion of the object, such as a removable panel. By example, a vehicle can be provided with a set of plastic panels that are readily installed upon an external surface, with one particular panel being specified for use during a predetermined period of time. Each panel may include a coating of the gain medium with scattering particles, or may itself be a body comprised of the gain medium and scattering particles (for example PPV and $TiO_2$).

Although the sphere 50 of FIG. 11 is shown as containing a volume of the medium 12, it is within the scope of the invention to construct the sphere from a polymer that is impregnated with the desired dye molecules and the scattering particles. Alternatively, the spheres could be small particles of a polymer such as PPV containing scattering particles. It is also within the scope of the invention to impregnate a porous material, such as certain glasses and solgels, with the gain medium.

It is also within the scope of the invention to employ an index of refraction contrast between, by example, a dye molecule solution contained within the pores and interstices of a host material, and the surrounding host material itself as the scattering phase. In this case the dye molecules provide the optical gain phase while the host material forms both the matrix and the scattering phases. In accordance with an aspect of this invention at least one dimension of a host/dye body may be made very small (e.g., tens or hundreds of micrometers in thickness or diameter) while exhibiting laser-like activity when suitably excited.

Figure 12A:
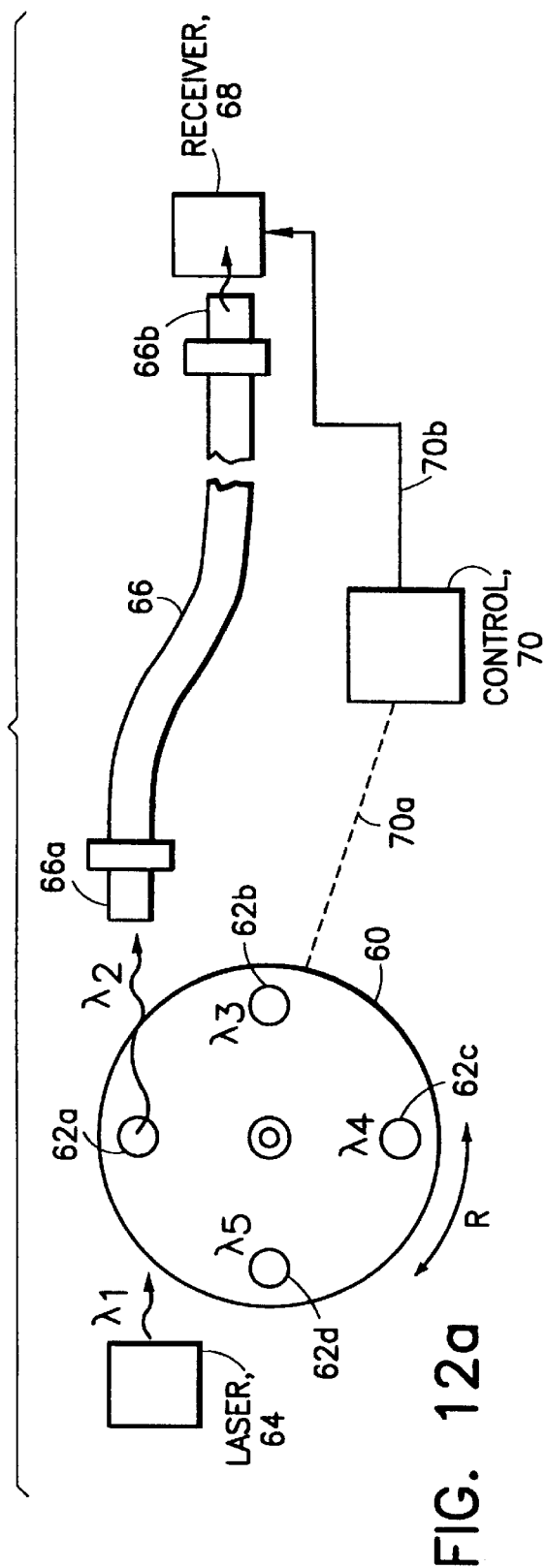
FIGS. 12a and 12b each illustrate an embodiment of the invention wherein the medium is employed to form a plurality of regions each of which emits a different output wavelengths in response to an input wavelength.

FIG. 12a illustrates an embodiment of the invention wherein the medium 12 is employed to form a plurality of regions 62a–62d upon a surface of a translatable, transparent substrate 60 for providing one of a plurality of different output wavelengths ($\lambda_2-\lambda_5$) in response to an input wavelength ($\lambda_1$). In the illustrated embodiment the substrate 12 has an axis of rotation such that a portion having the regions 62a–62d is positionable in the beam output from a laser 64. The emitted wavelength from a given one of the regions that is positioned within the beam is coupled into an optical fiber 66 having an input coupler 66a and an output coupler 66b. Optically coupled to the output coupler 66b is a radiation receiver 68. A controller 70 is mechanically coupled (70a) to the substrate 60 for rotating the substrate 60 for providing different ones of the emitted wavelengths to the receiver 68. The controller 70 is also electrically coupled (70b) to the receiver 68 for informing the receiver 68 of which wavelength is currently being emitted from the substrate 60. This arrangement enables a secure communication system to be constructed, wherein the laser 64 is modulated with information to be transmitted, and wherein the emitted wavelength is periodically and randomly changed by rotating the substrate 60.

As employed herein certain embodiments of this invention employ a relative motion between the gain medium 12 and a source of optical excitation. The motion may be generally linear or rotational, and can be achieved by physically moving one or both of the gain medium 12 and the optical excitation.

Figure 12B:
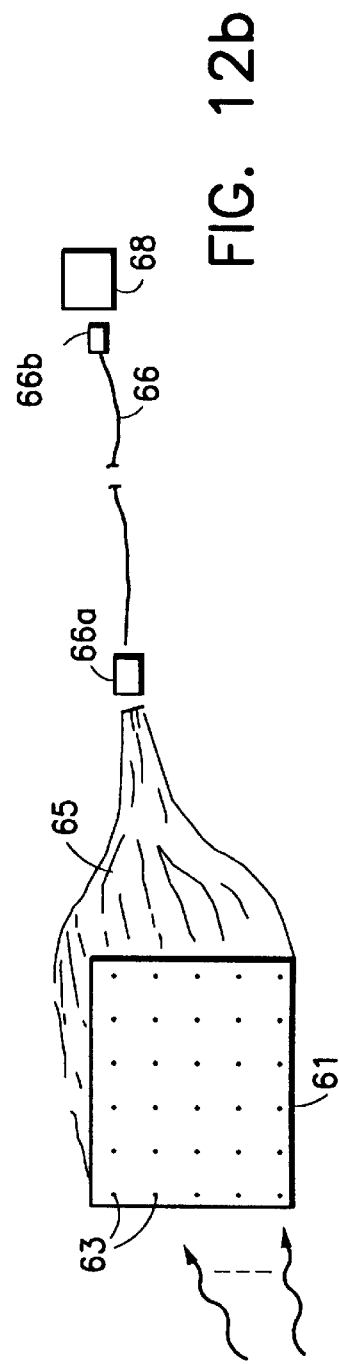

FIG. 12b illustrates a further embodiment of a communication system wherein a substrate 61 includes a plurality of region 63 (similar to the pixels illustrated in FIG. 9b). A bundle of fiber optic conductors 65 conveys light emitted from the region 63 to the coupler 66a, optical fiber 66, coupler 66b, and the receiver 68. In this embodiment a laser (not shown) scans different ones of the region 63 in accordance with a predetermined scanning algorithm while modulating information onto the scanned beam. The emission from one or more of the pixels is thereby transmitted to the receiver 68. So long as the receiver 68 is aware of the scanning algorithm used by the laser source no control connection is required between the transmitter and the receiver.

In other embodiments of the invention the substrates 60 or 61 can be employed as part of an optical source that selectively provides one of a plurality of different wavelengths in response to a single wavelength for use in, by example, chromatography instrumentation and laser color printer applications.

FIG. 13a illustrates an embodiment of this invention wherein the medium 12 is contained within an end portion 74 of a fiber optic 72, such as within the cladding layer, for providing a desired wavelength ($\lambda_2$) at a localized region. A laser 76 is employed for inputting a first wavelength ($\lambda_1$) into a second end of the fiber optic 72. One important,. but not limiting, application for this embodiment of the invention is in providing radiation having a predetermined wavelength to a localized region of tissue. An important aspect of this embodiment of the invention is the omnidirectional radiation pattern that can be achieved, although it is also within the scope of the this invention to include a focussing lens, or to use a self-focussing type of fiber, so as to provide a more directed beam.

FIG. 13b illustrates a further embodiment wherein a fiber 72b has the gain medium including scattering particles distributed within the cladding layer of the optical fiber 72. When inserted as a catheter within a structure such as a vein 73, and when pumped via a coupler 72a by the laser 76, the catheter is enabled to provide electromagnetic radiation within a predetermined range of wavelengths along a substantial length of the vein 73. This is useful in providing an optical source directly within a patient. The radiation can be selected so as to ablate tissue, cauterize, or any of a number of desired medical procedures. One advantage to this embodiment is that a single laser source 76 can be employed to provide, in combination with the novel catheter 72b, any one of a number of different desired wavelengths. Furthermore, the output of the catheter is inherently omnidirectional and thus may simultaneously irradiate a significant portion of the inner surface or surfaces of the vein 73 or other structure.

In this embodiment the radiation that is coupled from the core of the fiber 72b into the cladding is used to stimulate the emission from the gain material 12 that is contained within the cladding layer.

It is also within the scope of the invention to place a reflector at a terminal end of the catheter so as to reflect the laser radiation back along the length of the catheter so as to improve the efficiency of the generation of the desired wavelength.

FIG. 13c illustrates an embodiment of this invention wherein only a portion of the cladding layer has the gain medium of this invention so as to selectively irradiate only a portion of a surrounding structure. Alternately, a significant portion of the length of the cladding layer can include the gain medium 12, as in FIG. 13b, and the surface of the fiber catheter is then selectively masked so that the emission at $\lambda_2$, occurs at only one or more predetermined locations. In FIG. 13c, and also 13d, TB generally indicates a tissue boundary.

FIG. 13d illustrates an embodiment of this invention wherein the gain medium 12 is contained within the optical coupler 72a. In this case the wavelength $\lambda_2$ is generated external to the tissue boundary and is launched down the fiber 72b. For this embodiment a common source and fiber catheter can be employed, and the desired wavelengths are provided by placing a particular coupler 72a into the optical path.

FIG. 13e shows an embodiment of this invention wherein a terminal portion of the fiber 72b is provided with a structure 73 for converting a portion of the pump wavelength $\lambda_1$ into $\lambda_2$, and also for directing the radiation in a desired direction. In this embodiment the structure 73 includes a first portion 73a and a second portion 73b that are disposed at a predetermined angle one to another and to the terminal end of the fiber catheter 72b. A surface of the portion 73a includes a layer or coating of the gain material 12, while a surface of the region 73b can be made reflective, if desired.

FIG. 13f illustrates a further embodiment of this invention wherein the terminal portion of the fiber catheter 72b has a region 78 that is frosted or otherwise treated for causing the output radiation at wavelength $\lambda_2$ to be emitted in an omnidirectional manner at the terminal end.

In general, the invention provides a number of valuable medical applications for selectively treating and/or removing tissue. For example, the generated wavelength can be employed in a manner analogous to a scalpel so as to excise tissue.

It should also be realized that the fiber 72b is not required to be inserted within a structure, but can also be used to irradiate a surface portion thereof. By example, and referring to the embodiment of FIG. 13d, the fiber 72 be placed within a suitable supporting structure or jacket that enables same to be held in the hand, and a practitioner can then selectively apply the wavelength $\lambda_2$ that is emitted from the terminal end to a localized region of tissue, such as to the skin, or to an internal tissue during a surgical procedure.

Figure 14:
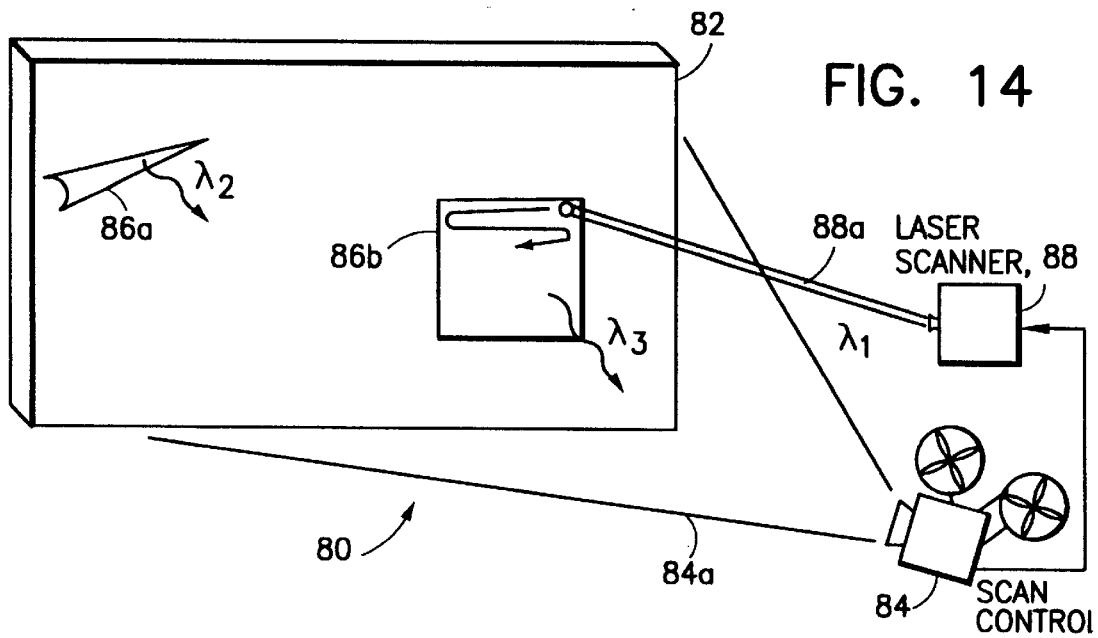
FIG. 14 illustrates an embodiment of this invention showing a system having a screen that is selectively coated with the medium, and a laser scanner for selectively causing the medium to emit a desired well defined wavelength.

FIG. 14 illustrates an embodiment of this invention showing a projection system 80 having a screen 82 that is uniformly or selectively coated with the medium 12. For example, only the regions 86a and 86b are coated with the medium 12. A conventional projector 84 is used for projecting light 84a conveying an image, such as motion picture, upon the screen 82. The system 80 further includes a laser scanner 88 that projects and rapidly scans a beam 88a having a first wavelength ($\lambda_1$) selectively upon the screen 82, and in particular upon the regions 86a and 86b. The regions 86a and 86b, when scanned by the beam 88a, emit a brilliant and substantially monochromatic light that is viewed by an audience. As a result, localized regions of the screen 82 are illuminated for providing special effects. The scan control signal can be provided from the projector 84 by recording. Same upon a track of the film or other image storage media that is used to project the image 84a.

By example, the dye coumarin 120 in combination with $Al_2O_3$ can be placed on a surface as coating or layer and will be substantially invisible to an observer until illuminated with a suitable excitation source. When illuminated, that portion of the coumarin/scattering particle layer emits a brilliant blue light that is non-saturable.

In a further embodiment of the invention the screen 82 is a billboard having an advertising message printed thereon, and the laser scanner is mounted for scanning the billboard at the selected regions 86a and 86b so as to cause selected portions of the advertising message to emit a brilliant, substantially monochromatic light having one or more wavelengths ($\lambda_2$ and $\lambda_3$).

In general, the medium 12 can be employed for a number of outdoor applications wherein it is desired to provide a readily visible or detectable marking or region. These applications include, but are not limited to, emergency markers, road barricades, marking predetermined pathways for robotic vehicles, and safety clothing for pedestrians and joggers. The medium 12 may also be employed as a component of a paint for marking roadway lanes and for printing road signs. For these applications automobiles, school buses and the like may be equipped with a source suitable for irradiating the markings that are comprised of the medium 12.

The markings could also be employed on automobiles to enhance the operation of automobile-mounted laser range finding systems used for collision avoidance. That is, the markings provide a strong and readily detectable return from an automobile when illuminated by a suitable laser range finder. Furthermore, the use of different wavelengths for different classes of vehicles enables target discrimination to be readily accomplished.

Figure 15A:
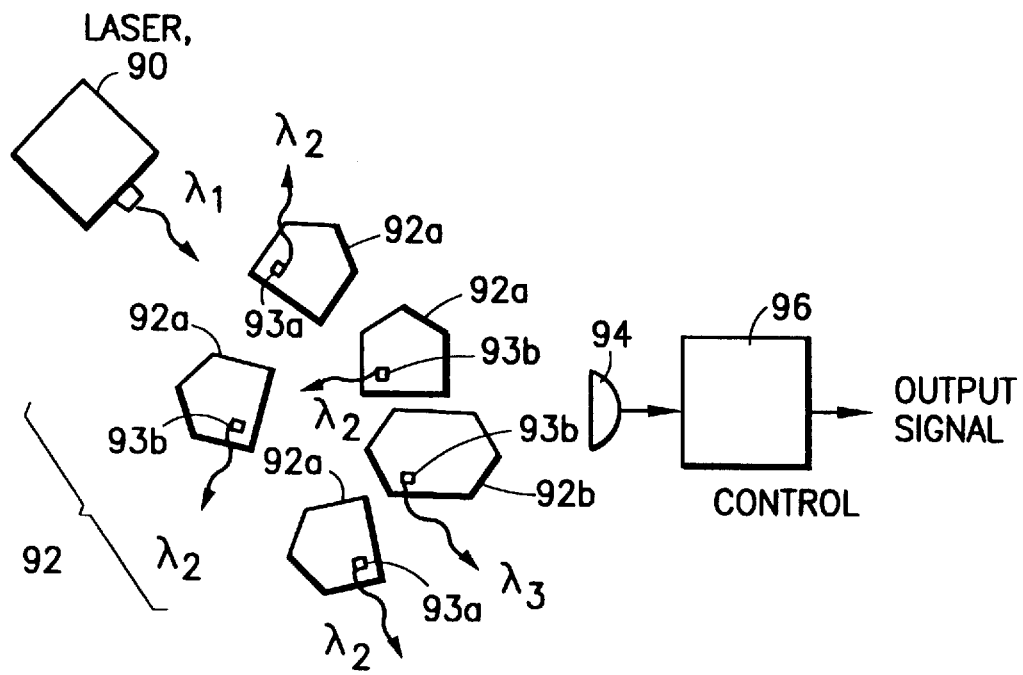
FIGS. 15a and 15b each illustrate an embodiment of this invention wherein a plurality of objects each include a coating comprised of the medium, a laser for illuminating the objects, and a detector for detecting the wavelength emitted by the coatings.

FIG. 15a illustrates an embodiment of this invention wherein a plurality of objects 92a–92b each include a coated region 93a–93b comprised of the medium 12. A laser 90 emits a first wavelength ($\lambda_1$) for illuminating the objects 92. A detector 94 is positioned for detecting at least one of the wavelengths ($\lambda_2$ and $\lambda_3$) emitted by the coated regions. In the illustrated example, the objects 92a are all identical and all emit at the same wavelength $\lambda_2$. The object 92b emits at the wavelength $\lambda_3$. This arrangement is useful in, for example, sorting and quality control operations wherein it is desirable to provide a homogeneous population of objects by detecting and removing dissimilar objects from the population.

For example, and for a given operation where it is desired to provide only the objects 92a, the detector 94 may be provided with a filter or some other means for passing only the wavelength ($\lambda_3$). The output of the detector 94 is connected to a control unit 96 that generates an output signal in response to a detection of the wavelength $\lambda_3$. The output signal can be employed to generate an audio or visual alarm signal, or to activate a diverter mechanism for automatically removing the object 92b. Each item can be encoded with more than one coated region (for example each may include three regions) enabling greater selectivity.

Figure 15B:
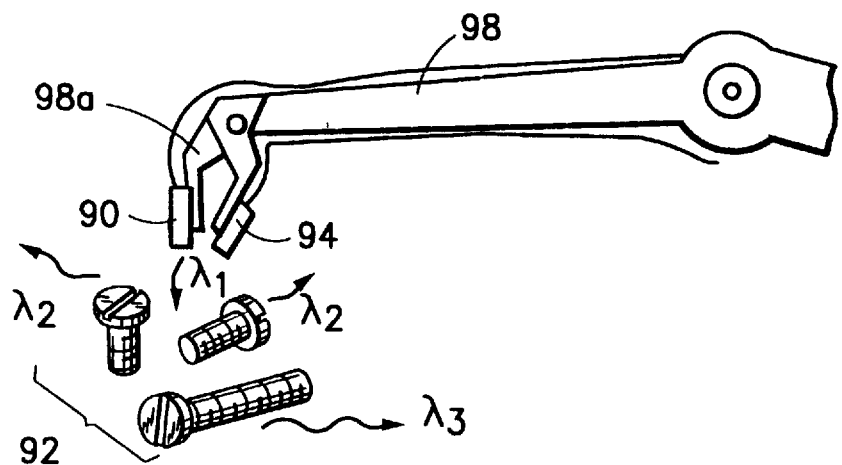

FIG. 15b illustrates a further embodiment wherein a robot manipulator arm 98 has an end effector portion 98a for grasping objects, such as a plurality of bolts that comprise the set 92. In this embodiment of the invention the laser 90, such as a laser diode, is provided at or near the end effector portion 98a for irradiating the objects that are disposed in proximity to the end effector. Alternately, the laser 90 may be remotely provided and the output thereof conveyed through an optical fiber to the end effector portion 98a. The detector 94 is similarly disposed for detecting the emitted radiation from the objects that are illuminated by the laser 90. In the illustrated embodiment bolts of a first length include a coated region comprised of the medium 12 so as to emit radiation of a first wavelength, while bolts of a second length include a coated region comprised of the medium 12 so as to emit radiation of a second wavelength. A manipulator controller (not shown) is responsive to the detected radiation to select or avoid an object emitting a particular wavelength.

It can be appreciated that this embodiment of the invention does not require complex image processing software to distinguish the objects one from another. Instead, the objects are inherently distinguishable due to the wavelength that each emits.

Figure 16:
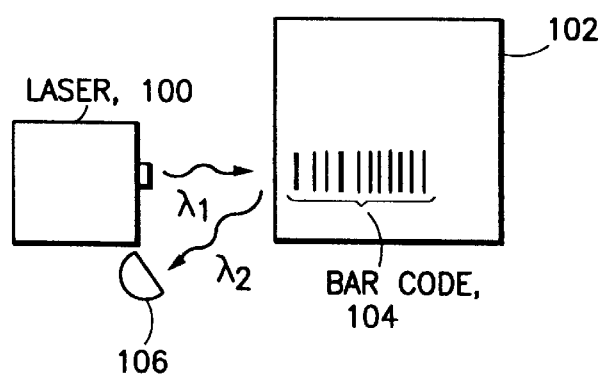
FIG. 16 illustrates an embodiment of this invention wherein the medium is employed to form an indicia, specifically a bar code, upon a surface of an object.

FIG. 16 illustrates an embodiment of this invention wherein the medium 12 is employed to form an indicia, specifically a bar code 104, upon a surface of an object 102. In response to illumination with a wavelength $\lambda_1$ by a laser 100 the bar code 104 emits a brilliant, substantially monochromatic light at a wavelength $\lambda_2$. A detector 106 is responsive to the emitted light and is coupled to a conventional bar code reader (not shown). This embodiment of the invention provides a bar code having a superior visual contrast. Furthermore, this embodiment of the invention enables wavelength encoding of the bar code information. That is, all or a portion of the bar code information can have one meaning at a first wavelength and a modified or completely different meaning at a second wavelength. In this case the bar code reader preferably includes a wavelength discrimination means, such as filters and/or a grating, for also identifying and detecting the emitted wavelength. It is also within the scope of the invention to select a medium 12 that is substantially invisible to an observer so as to provide "invisible" bar coding when not irradiated.

Figure 17:
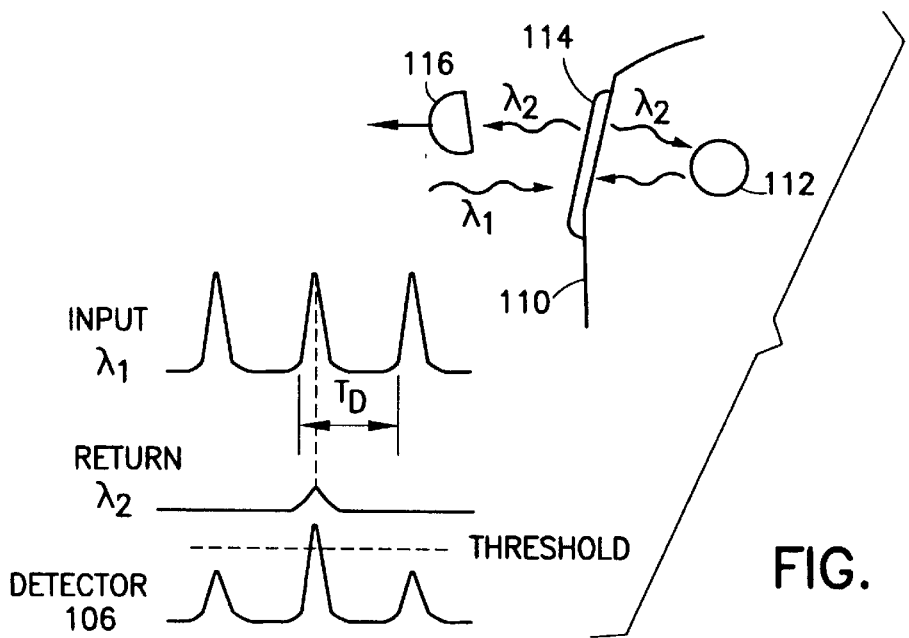
FIG. 17 illustrates an embodiment of this invention wherein the medium is applied as a coating (solid or semi-solid) to an object capable of internally transmitting a wavelength or wavelengths that are emitted by the coating.

FIG. 17 illustrates an embodiment of this invention wherein the medium 12 is applied as a coating 114 to an object 110 that is capable of internally transmitting a wavelength or wavelengths that are emitted by the coating 114. This embodiment exploits the short pulse and fast response times of the medium 12. In response to a pulsed laser source that emits a wavelength $\lambda_1$ the coating 114 emits light with the wavelength $\lambda_2$. The emitted light propagates into the object 110. In response to a discontinuity (change in the index of refraction), such as a body 112 that is located within the object 110, a portion of the wavelength $\lambda_2$ is reflected back towards the surface having the coating 114. The reflected portion passing through the coating 114 seeds the dye molecules contained within the coating 114, thereby enhancing the output of the coating 114 at the wavelength $\lambda_2$ when simultaneously illuminated with a pulse from the pulsed laser source. A detector 116 is positioned for detecting the amplitude of the return pulse at the wavelength $\lambda_2$. The return pulse conveys temporal and spatial information concerning the internal structure of the object 110. By example, this embodiment of the invention can be used in a tomography application wherein it is desired to detect an object within the human body. It is also within the scope of the invention to use a plurality of coatings 114 at different surface regions, and to employ triangulation techniques to accurately locate the body 112.

As in the embodiment of FIG. 10, the coating 114 can be applied to a transparent substrate (not shown) prior to application to the surface of object 110. Also, the coating 114 can be comprised of a plurality of different regions each emitting at a different wavelength. In this case, the detector 116 is made responsive to the different wavelengths through the use of, by example, suitable filters and/or a grating.

In general, the inter-pulse spacing ($T_0$) between the input pulses, in combination with a delay in detecting the emitted wavelength ($\lambda_2$), gives information concerning the depth and/or location of the body 112 from the surface of the object 110.

Figure 18:
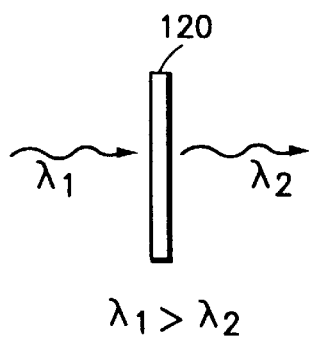
FIG. 18 illustrates an embodiment of this invention wherein the medium is employed to up-convert a first wavelength to a second, shorter wavelength.

FIG. 18 illustrates an embodiment of this invention wherein the medium 12 is employed to up-convert a first-wavelength ($\lambda_1$) to a second, shorter wavelength ($\lambda_2$). By example, the medium 12 is provided as a thin layer or volume 120 and operates by a strong, resonantly enhanced two photon absorption process. One suitable dye for this application is DCM used in combination with scattering particles as described above. When pumped at a wavelength of 735 nm the medium 12 emits at 630 nm.

Figure 19:
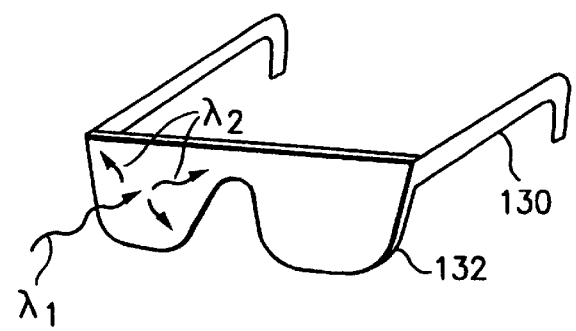
FIG. 19 illustrates an embodiment of the invention wherein the medium is employed as a coating on the lens of an eye-glass for providing laser eye protection.

FIG. 19 shows an embodiment of the invention wherein the medium 12 is provided upon or within the lens material of a laser eye protector 130. This embodiment provides non-saturable eye protection wherein the incident laser radiation is converted to the optical signal at the second wavelength.

When the medium 12 is provided as a thin layer a significant portion of the emitted energy is directed transversely within the layer. As a result, a significant portion of the input energy is directed away from the eye.

Due to the presence of the scattering particles a volume of the medium 12 may appear to be substantially opaque. However, when applied as a thin layer, in accordance with an aspect of this invention, an significant amount of light is able to pass through the layer. This ability to use thin coatings or layers of the medium 12 makes the use of the medium 12 suitable for a number of applications that would be difficult or impossible to achieve if the smallest dimension were required to be much larger than the scattering length.

By example, a substrate material can be a textile that is treated with the medium 12. In response to incident laser radiation from, by example, a hostile source, a significant portion of the power of the incident radiation is converted to an emission at one or more other wavelengths. This provides the wearer of the textile with a degree of protection from injury due to the hostile laser radiation source.

Although described thus far primarily in the context of a laser dye in combination with scattering particles that is illuminated or irradiated by a laser source, it should be appreciated that in other embodiments of the invention a chemi-luminescent material can be employed in combination with the dye and scattering particles. This removes the requirement that an optical source be employed to pump the dye molecules, so long as the chemi-luminescent material provides sufficient energy.

One suitable chemi-luminescent system includes an alkalo-metal base (e.g., sodium hydroxide), hydrogen peroxide, a non-hydroxylic solvent (e.g., dibutyl phthalate), an oxalate ester (e.g., bis-trichlorophenyl oxalate), and a laser dye to be excited (e.g. a suitable rhodamine) in combination with a suitable scattering phase (nanoparticles, voids, etc.).

Electrically stimulated gain mediums are also within the scope of this invention. For example, the material PPV can be used in combination with scattering particles, thereby eliminating a requirement for providing a dye. The PPV can be either electrically driven or optically driven to provide the laser-like optical emission, or to provide a broadening and shifting of the PPV emission.

Furthermore, it is known that the fluorescence of some dyes, known generally as electrochromic dyes, can be tuned by the application of an electric field on the order of 1K V/cm. As such, the use of an electrochromic dye in combination with the scattering particles enables the emitted wavelength to be tuned over a range of wavelengths. Due to the thinness of the film, in accordance with an aspect of the invention, only a relatively modest electrical potential is required (for example, one volt) to generate the required electric field potential.

In general, due to the very small dimensions of the gain medium regions that are made possible by the teaching of this invention (for example, tens of wavelengths) the volume of medium that is required to obtain the desired, substantially monochromatic emission is on the order of the size of cell structures. This enables a microscopic amount of the medium 12 to be used to observe and/or influence the cell operation.

In view of the foregoing description of a number of embodiments of this invention, it should be realized that modifications to these embodiments can be made, and that these modifications are all within the scope of the teaching of the invention. By example, the use of the invention is not limited to only those specific applications which have been expressly described above, nor is the teaching of this invention limited to only the specific materials, concentrations, wavelengths, and the like that have been described in detail above.

Figure 20A:
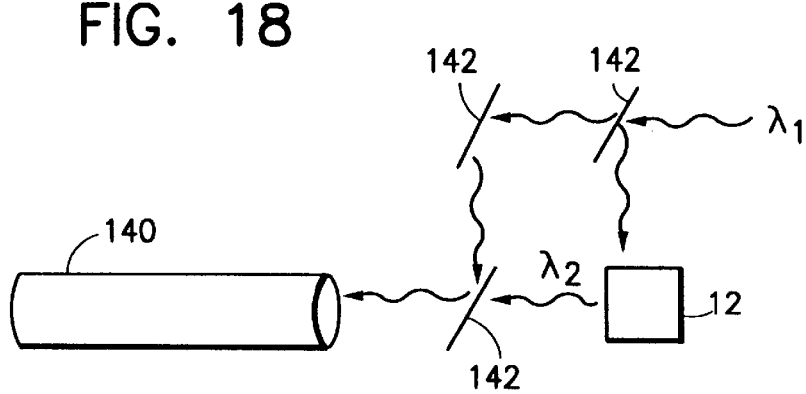
FIGS. 20a–20c illustrate the use of the medium in a non-linear Raman scattering embodiment.
Figure 20B:
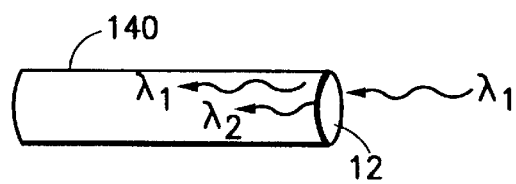
Figure 20C:
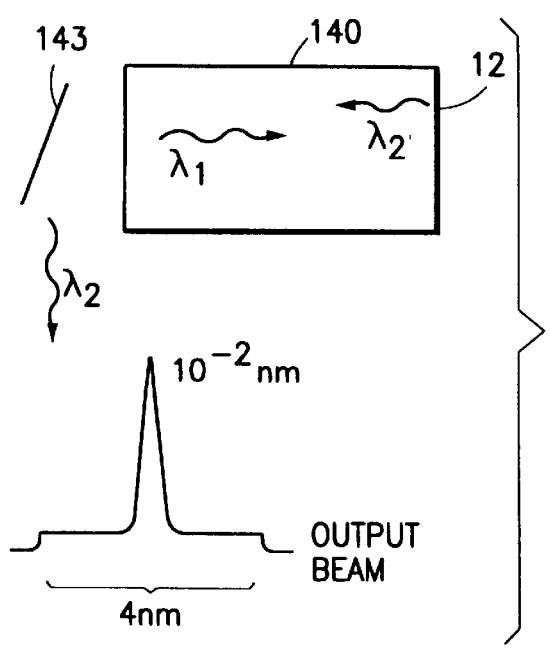

By example, the invention can be employed in an embodiment that obtains gain through a non-linear process by stimulated or spontaneous Raman scattering. This is illustrated in FIGS. 20a–20c. In FIG. 20a a Raman scattering system includes a non-linear first gain medium (a gas such as methane or $CS_2$) contained within an enclosure 140. Typically, high input powers are required to stimulate emission from the gain medium. In the illustrated embodiment a pump wavelength ($\lambda_1$) is provided to a plurality of mirrors 142 which direct most of the pump into the enclosure 140. Some of the pump radiation is diverted to a cell, coating or body that includes the medium 12. The medium 12 provides a second wavelength ($\lambda_2$) which acts as a seed to effectively lower the threshold of the Raman scattering amplifier embodied within the enclosure 140. This is a non-linear, as opposed to a linear, gain mechanism.

In the embodiment of FIG. 20b the medium 12 is provided on an input face of the enclosure 140 thereby simplifying the embodiment of FIG. 20a.

In the embodiment of FIG. 20c the medium 12 is provided on a back face of the enclosure 140. In this configuration the medium 12 responds to the pump wavelength by emitting the seed radiation back into the enclosure 140. An external dichromic mirror 143 directs the second wavelength to a desired optical path. In this embodiment the output beam from the Raman scattering amplifier exhibits an approximately four nanometer wide spectrum having a very narrow ($10^2$ nm) peak.

As a further example of the utility of this invention reference is made to FIG. 21 which illustrates a small particle or a sphere having a nominal diameter of, by example, approximately 30 microns. The sphere includes the medium 12 either on or within a surface region thereof or distributed throughout the volume of the sphere. An excitation source provides a first wavelength which is focused down to approximately the diameter of the sphere. In this embodiment the sphere absorbs the input wavelength and, due to the rapid emission properties of the medium 12, almost immediately emits the second wavelength. That is, in that the medium 12 is substantially non-saturable, the sphere is enabled to repeatedly receive pulses of input radiation. It can be shown that a significant force is exerted on this sphere by this process, in that the emission from the sphere is isotropic. As such, and if the sphere is suspended in an aerosol or a liquid, the sphere will move away from the input pump beam at a high velocity without significant heating.

It can be appreciated that this embodiment of the invention provides an accelerator for particles on the order of tens of micrometers in diameter. The resultant particle stream can be used for material processing, such as cutting and surface erosion. The resultant particle stream can also be used to deliver small quantities of a substance, such as a pharmaceutical product, to a specified region within an object.

This embodiment takes advantage of the ability of the medium 12 to isotropically and very rapidly lase away the energy received from the input pump beam.

FIG. 22 is a cross-sectional view, not to scale, of a polymer-based, electrically powered light emitting device 150 that benefits from the emission broadening and shifting that is made possible by this invention. The emission broadening and shifting aspect is clearly seen when contrasting trace "a" of FIG. 1 to trace "b" of FIG. 1.

The device 150 includes a first electrode 152, a region 153 comprised of the gain medium of this invention, and a substantially transparent second electrode 154. A source of electrical power (AC or DC) is schematically shown as a battery 156 that is coupled across the electrodes 152 and 154.

The region 153 may be comprised of layer (having a thickness within the range of approximately 1,000 Å to approximately 5,000 Å) of an organic polymer such as polyphenelyne vinylene (PPV) that has scattering particles of suitable dimensions (for example 30 Å to 56 Å) added in accordance with this invention. The electrode 152 may be comprised of oxidized aluminum having the region 153 spin-coated thereon. The transparent electrode 154 may be comprised of indium-tin-oxide (ITO).

In operation, the injection of charge carriers from the battery 156 causes an emission from the PPV in a known manner. In accordance with this invention, the scattering particles cause a broadening and a shifting of the PPV emission, as indicated in FIG. 1, trace "a".

It is also within the scope of this invention to add a suitable dye to the region 153 that absorbs and re-emits the PPV emission.

FIG. 23 is a cross-sectional view, not to scale, of an electrically operated optical source 160 that is constructed in accordance with an aspect of this invention, wherein the gain medium 12 of this invention is applied as a coating 164 to an emission face of a semiconductor laser diode 162 to provide an emission at a wavelength ($\lambda_2$) that differs from the fundamental emission wavelength ($\lambda_1$) of the laser diode. A suitable source of electrical power, shown schematically as a battery 166, is applied across a junction of the laser diode 162 in a conventional manner. The laser diode 162 can be operated in a gain switched mode, and may be a transverse emission type, as illustrated, or a vertical emission type.

This embodiment of the invention enables a single type of laser diode to be customized so as to provide one of a number of different and desired output wavelengths, as a function of the optical properties of the selected gain medium of the coating 164.

FIG. 24a is an elevation view, not to scale, and FIG. 24b is a top view, not to scale, showing an embodiment of this invention wherein the gain medium 12 of this invention is employed as a spectral converter for pumping a second gain medium 172, such as a flowing dye solution or a laser rod, so as to tune a pump wavelength ($\lambda_1$) to the requirements of the second gain medium. This pump source 170 thus employs a coating or layer 174 of the gain medium 12 that is interposed between an optical pump 176, for example a flash lamp, and the second gain medium 172. The coating or layer 174 provides an emission wavelength ($\lambda_2$) that is selected as being optimal or nearly optimal for the second gain medium 172. This embodiment of the invention thus optimizes the optical pumping wavelength for the second gain medium 172, and enables a single type of pump source 176 to be used with a variety of second gain mediums.

It should be appreciated that in view of the numerous applications and embodiments made possible by this invention, the teaching of this invention is not intended to be limited in scope to only the disclosed applications and embodiments.

For example, it is also within the scope of the invention to employ one or more additives to the gain medium to improve the performance. For example, a dye triplet-quencher, such as COT or hexatriene, can be used in combination with the dye and scattering particles. This enables quasi-continuous operation of the medium 12. Also by example, a dye life extender, such as DABCO, can be employed as an additive. Also by example, a dye solubilizing additive, such as ARQUAD, can be employed. For a system wherein the gain medium is incorporated into an acrylic plastic, such as PMMA, the solubilizing additive HEMA can be employed to enhance the solubility of the selected dye in the plastic.

It should be apparent that this invention teaches a gain medium that is a multi-phase system, wherein: a first phase is an electromagnetic radiation emission and amplifying phase; a second phase is an electromagnetic radiation scattering phase; and a third phase is a transparent matrix phase.

By example only, the emitting and amplifying phase may comprise one or more types of dye molecules and/or semiconductor nanocrystals; the scattering phase may be comprised of oxide particles such as $Al_2O_3$, $TiO_2$, $SiO_2$, or $Fe_2O_3$, or metal particles such as Au or Ag; and the matrix phase may comprise a liquid such as methanol, ethylene glycol, DMSO, or $H_2O$, or a semiliquid such as a cream, gel, or an epoxy, or a solid such as polymer selected from, by example, PMMA, PPV, polyester, or polystyrene.

The scattering phase is generally embodied as high index of refraction contrast scattering sites such as nanoparticles of an oxide, metal, or semiconductor. The scattering sites can also be embodied as voids within a porous matrix or substrate, and/or as point defects and discontinuities within the matrix, either alone or in combination with the particles.

With respect to the use of semiconductor nanocrystals, reference can be had to a publication entitled "Synthesis and Characterization of Nearly Mono disperse CdE (E=S, Se, Te) Semiconductor Nanocrystallites", C. B. Murray et al., J. Am. Chem. Soc. 1993, 115, 8706–8715, which teaches a method to produce semiconductor nanocrystals or crystallites, from approximately 12 Å to approximately 115 Å in diameter, which are suitable for use in practicing this invention.

In general, a number of Group II-VI and Group III-V direct gap semiconductors can be employed, as can an indirect gap material such as porous silicon.

In some embodiments of the invention the emitting and amplifying and the also the scattering phases may be the same phase, as when semiconductor particles are employed.

A smallest dimension of a body, layer or region comprised of the gain medium may be less than or on the order of a scattering length associated with the scattering phase. The gain medium can be embodied within a monolithic, one piece structure such as sheet, block, or sphere, or can be disposed as one or more layers or regions within or upon a substrate. Suitable substrates include glasses, dielectrics, polymers, a layer of the gain medium itself, tissue, semiconductor materials, textiles, and metals.

A further aspect of this invention is a method of broadening and shifting a band of emission wavelengths from a dye, polymer, semiconductor and other sources of emission by the steps of: (a) providing a sample comprised of an optical emitter, such as one or more types of dye molecules or a polymer, in combination with a plurality of scattering particles or sites and also a medium that is substantially transparent to the band of emission wavelengths; (b) inputting energy into the sample with an electrical current or with electromagnetic radiation having wavelengths suitable for generating an emission from the optical emitter; and (c) broadening and shifting a band of emission wavelengths from the optical emitter by scattering the emission with the scattering particles or sites.

It should also be evident that it is within the scope of this invention to employ the electromagnetic radiation that is emitted from the gain medium as a heat source.

Furthermore, and as was previously indicated, the teaching of this invention is not intended to be limited in scope by any specific explanation of, or theoretical rationale for, the underlying electro-physical-optical processes that result in the generation of laser-like activity within the medium 12.

Thus, the teaching of this invention is intended to be given a scope commensurate with the scope of the claims that follow.

What is claimed is:

1. An object, comprising:

a substrate; and coupled to said substrate, a wavelength encoded region comprising a plurality of electromagnetic radiation emitter and amplification portions each of which is optically coupled to a scattering portion for increasing a residence time of the electromagnetic radiation within the region, said wavelength encoded region emitting, when energized by incident light, a plurality of wavelengths that identify said object.

2. An object as in claim 1, wherein at least said wavelength encoded region is covered by a transparent protective layer or coating.

3. An object as in claim 1, wherein at least said wavelength encoded region is encapsulated.

4. A system for generating and detecting an optical signal, comprising:

a region comprised of an electromagnetic radiation emitter and amplification material that is optically coupled to a scattering material for increasing a residence time of electromagnetic radiation within the region;

an optical source for illuminating said region with electromagnetic radiation for stimulating an emission from said emitter and amplification material such that said emitter and amplification material, in cooperation with said scattering material, provides an optical signal comprised of an emission of a spectrally collapsed band of wavelengths; and an optical detector for detecting the emission.

5. A system as in claim 4, wherein the region is disposed on individual ones of a plurality of substrate bodies for emitting an optical signal that distinguishes one substrate body from other substrate bodies, and wherein said optical detector has an output coupled to means for segregating the plurality of substrate bodies into two or more groups of substrate bodies in accordance with the detected emissions from the substrate bodies.

6. An system as in claim 5, wherein at least said region of each substrate body is covered by a protective layer or coating.

7. An system as in claim 5, wherein at least said region of each substrate body is encapsulated.

8. A method for identifying individual ones of items provided as an assemblage of items, comprising steps of:

providing a wavelength encoded region that forms a portion of each item, the wavelength encoded region comprising a plurality of electromagnetic radiation emitter and amplification portions each of which is optically coupled to a scattering portion for increasing a residence time of electromagnetic radiation within the region;

illuminating individual ones of the items with electromagnetic radiation for stimulating emissions from said plurality of emitter and amplification portions such that each emitter and amplification portion, in cooperation with said scattering portion, emits a distinctive narrow band of wavelengths;

detecting the emission of the distinctive narrowband of wavelengths from an item; and identifying the item in accordance with the detected emission.

9. A method as in claim 8, and further comprising a step of segregating an identified item from the assemblage of items.

10. A method for generating and detecting an optical signal, comprising steps of:

providing a region comprised of an electromagnetic radiation emitter and amplification material that is optically coupled to a scattering material for increasing a residence time of electromagnetic radiation within the region;

illuminating the region with electromagnetic radiation for stimulating an emission from said emitter and amplification material such that said emitter and amplification material, in cooperation with said scattering material, provides an optical signal comprised of an emission of a spectrally collapsed band of wavelengths; and detecting the emission.

11. A method as in claim 10, wherein the region is provided so as to disposed on individual ones of a plurality of substrate bodies for emitting an optical signal that distinguishes one substrate body from other substrate bodies, and further comprising a step of segregating the plurality of substrate bodies into two or more groups of substrate bodies in accordance with the detected emissions from the substrate bodies.

12. A method as in claim 11, wherein at least the region of each substrate body is covered by a protective layer or coating such that the step of illuminating illuminates the region through the protective layer or coating.

13. A method as in claim 11, wherein at least the region of each substrate body is encapsulated such that the step of illuminating illuminates the region through the encapsulation.

* * * * *